United States Patent [19]

Gouin d'Ambrieres et al.

[11] 4,349,545
[45] Sep. 14, 1982

[54] NOVEL ERYTHROMYCIN A DERIVATIVES

[75] Inventors: Solange Gouin d'Ambrieres, Paris; André Lutz, Strasbourg; Jean-Claude Gasc, Bondy, all of France

[73] Assignee: Roussel Uclaf, Paris, France

[21] Appl. No.: 223,368

[22] Filed: Jan. 8, 1981

[30] Foreign Application Priority Data

Jan. 11, 1980 [FR] France .................................. 80 00566

[51] Int. Cl.³ .......................... A61K 31/70; C07H 17/08
[52] U.S. Cl. ........................................ 424/180; 536/7.4
[58] Field of Search ............................ 536/9; 424/180

[56] References Cited

U.S. PATENT DOCUMENTS

| | | | |
|---|---|---|---|
| 3,869,444 | 3/1975 | Freiberg | 536/9 |
| 4,016,263 | 4/1977 | Wetzel et al. | 536/9 |
| 4,256,738 | 3/1981 | Woitun et al. | 536/9 |

*Primary Examiner*—Blondel Hazel
*Attorney, Agent, or Firm*—Hammond & Littell, Weissenberger and Muserlian

[57] ABSTRACT

Novel erythromycin derivatives in the syn form or anti form or mixtures of the syn and anti forms of the formula

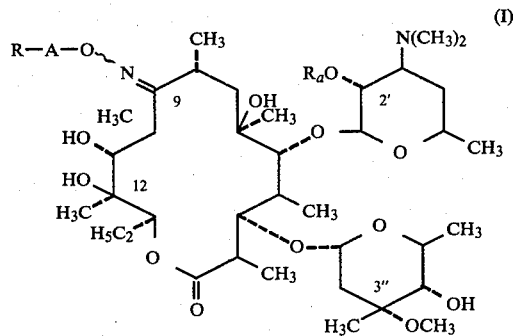

wherein A is a linear or branched alkylene of 1 to 6 carbon atoms, R is selected from the group consisting of optionally substituted alkoxy of 1 to 6 carbon atoms, optionally substituted alkenyloxy and alkynyloxy of 2 to 6 carbon atoms, optionally substituted alkylthio of 1 to 6 carbon atoms, optionally substituted alkenylthio and alkynylthio of 2 to 6 carbon atoms with the thio group optionally oxidized to the sulfoxide or sulfone form, optionally substituted aryloxy and arylthio, optionally substituted aralkyloxy and arylalkylthio, the thio derivatives optionally oxidized to sulfoxide or sulfone,

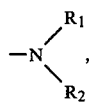

optionally substituted quaternary ammonium group, halogen, optionally substituted 1,2-epoxyethyl and the group resulting from opening of the epoxy with a nucleophilic reactant,

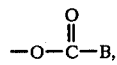

a free or protected formyl, —COOR', thiocyanate, —CN, acyl and carbamoyl, $R_1$ and $R_2$ are individually selected from the group consisting of hydrogen, and optionally substituted alkyl of 1 to 6 carbon atoms or taken together with the nitrogen atom to which they are attached form an optionally substituted, optionally unsaturated heterocycle which can contain another heteroatom, B is selected from the group consisting of optionally substituted alkyl and alkoxy of 1 to 6 carbon atoms, optionally substituted aryl and aryloxy and optionally substituted aralkyl and aralkoxy of 1 to 6 alkyl carbon atoms, R' is selected from the group consisting of hydrogen, a cation and an ester group, $R_a$ is selected from the group consisting of hydrogen and acyl of an organic carboxylic acid of 1 to 18 carbon atoms and their non-toxic, pharmaceutically acceptable acid addition salts having very good antibiotic activity and their preparation.

18 Claims, No Drawings

NOVEL ERYTHROMYCIN A DERIVATIVES

STATE OF THE ART

Erythromycin and derivatives thereof are described in U.S. Pat. No. 3,681,326, No. 3,855,203 and No. 3,869,445, German Pat. No. 2,515,076 and No. 2,515,077, French Pat. No. 2,201,874 and Chem. Abs., Vol. 87 (1977), p. 657, No. 102,607s and Chem. Abs., Vol. 91 (1979), p. 632, 123967 g.

OBJECTS OF THE INVENTION

It is an object of the invention to provide the novel compounds of formula I and their non-toxic, pharmaceutically acceptable acid addition salts and a process for their preparation.

It is another object of the invention to provide novel antibacterial compositions and a novel method of combatting bacterial infections in warm-blooded animals.

These and other objects and advantages of the invention will become obvious from the following detailed description.

THE INVENTION

The novel erythromycin derivatives of the invention are compounds in the syn form or anti form or mixtures of the syn and anti forms of the formula

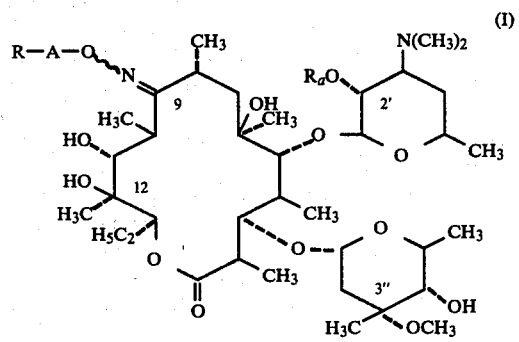

wherein A is a linear or branched alkylene of 1 to 6 carbon atoms, R is selected from the group consisting of optionally substituted alkoxy of 1 to 6 carbon atoms, optionally substituted alkenyloxy and alkynyloxy of 2 to 6 carbon atoms, optionally substituted alkylthio of 1 to 6 carbon atoms, optionally substituted alkenylthio and alkynylthio of 2 to 6 carbon atoms with the thio groups optionally oxidized to the sulfoxide or sulfone form, optionally substituted aryloxy, and arylthio, optionally substituted aralkyloxy and arylalkylthio, the thio derivatives optionally oxidized to sulfoxide or sulfone,

optionally substituted quaternary ammonium group, halogen, optionally substituted 1,2-epoxyethyl and the group resulting from opening of the epoxy with a nucleophilic reactant,

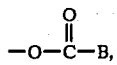

a free or protected formyl, —COOR', thiocyanate, —CN, acyl and carbamoyl, $R_1$ and $R_2$ are individually selected from the group consisting of hydrogen and optionally substituted alkyl of 1 to 6 carbon atoms or taken together with the nitrogen atom to which they are attached form an optionally substituted, optionally unsaturated heterocycle which can contain another heteroatom, B is selected from the group consisting of optionally substituted alkyl and alkoxy of 1 to 6 carbon atoms, optionally substituted aryl and aryloxy and optionally substituted aralkyl and aralkoxy of 1 to 6 alkyl carbon atoms, R' is selected from the group consisting of hydrogen, a cation and an ester group, $R_a$ is selected from the group consisting of hydrogen and acyl of an organic carboxylic acid of 1 to 18 carbon atoms and their non-toxic, pharmaceutically acceptable acid addition salts.

Examples of alkylene groups of A are methylene, ethylene, propylene, butylene, pentamethylene, hexamethylene and branched alkylenes of the formula

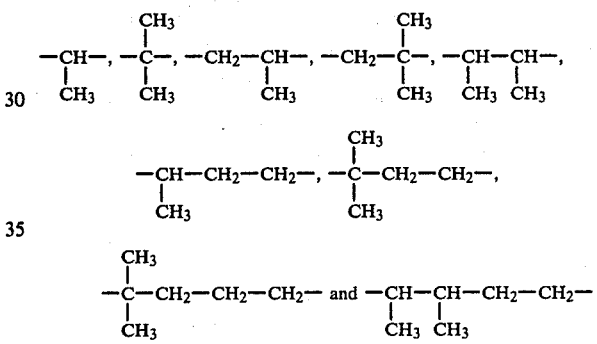

Examples of groups of R are (A) alkoxy of 1 to 6 carbon atoms such as methoxy, ethoxy, propyloxy, isopropyloxy, n-butyloxy, isobutyloxy, tert.-butyloxy, n-pentyloxy, isopentyloxy, sec-pentyloxy, tert.-pentyloxy, neopentyloxy, n-hexyloxy, sec-hexyloxy and tert.-hexyloxy; (B) alkylthio of 1 to 6 carbon atoms such as methylthio, ethylthio, propylthio, isopropylthio, n-butylthio, iso-butylthio, tert.-butylthio, n-pentylthio, isopentylthio, sec.-pentylthio, tert.-pentylthio, neopentylthio, n-hexylthio, sec.-hexylthio and tert.-hexylthio and the oxidized thio derivatives such as mehylsulfinyl and methylsulfonyl; (C) alkenyloxy and alkenylthio of 2 to 6 carbon atoms such as vinyloxy, 1-propenyloxy, allyloxy, 1-butenyloxy, 2-butenyloxy, 3-butenyloxy, 2-methyl-1-butenyloxy, pentenyloxy, hexenyloxy and 3-methyl-2-butenyloxy and the corresponding sulfur derivatives and oxides thereof; (D) and alkynyloxy and alkynylthio of 2 to 6 carbon atoms such as ethynyloxy, propargyloxy, propynyloxy, butynyloxy, pentynyloxy, hexynyloxy, ethynylthio, propargylthio, propynylthio, butynylthio, pentynylthio and hexynylthio and the oxidized derivatives thereof.

Examples of further groups of R are (E) aryloxy and arylthio such as phenoxy, thienyloxy, furyloxy, thiazolyloxy, thiadiazolyloxy, oxazolyloxy, tetrazolyloxy, pyrrolyloxy, imidazolyloxy, pyranzolyloxy, isothiazolyloxy, isoxazolyloxy, triazolyloxy, thiatriazolyloxy, pyridyloxy as well as the condensed ring systems benzothienyloxy, benzofuryloxy, indolyloxy and benzimidazolyloxy and the corresponding thio compounds optionally oxidized such as phenylthio, phenylsulfonyl and phenylsulfinyl; and (F) aralkoxy and aralkylthio of 1 to 6 alkyl carbon atoms such as benzyloxyl, phenethoxy, phenylpropoxy, thienylmethoxy, thienylethoxy, thienylpropoxy, furfuryloxy, furylethoxy, furylpropoxy, thiazolylmethoxy, thiazolylethoxy, tetrazolylmethoxy, thiadiazolylmethoxy, thiadiazolylethoxy and the corresponding thio derivatives optionally oxidized to the sulfonyl or sulfoxide form.

The optional substituents for groups (A) to (F) includes at least one substituent selected from the group consisting of hydroxy, methoxy, ethoxy, propoxy, isopropoxy, butoxy, sec-butoxy, tert.-butoxy, vinyloxy, allyloxy, ethynyloxy, propargyloxy, methylthio, ethylthio, propylthio, isopropylthio, n-butylthio, sec.-butylthio, tert.-butylthio, vinylthio, allylthio, ethynylthio, propargylthio, fluorine, chlorine, bromine, iodine, —NH$_2$, methylamino, dimethylamino, diethylamino, 1-piperazinyl, 4-methyl-piperazin-1-yl, 1-piperidinyl, 1-pyridinium, N-morpholino, 1-pyrrolyl, pyrrolidinyl, imidazolyl, 1-pyridazinium and 1-pyrimidinium.

The optional substitutents for groups (E) and (F) may also be selected from the group consisting of methyl, ethyl, propyl, carbamoyl, aminomethyl, dimethylaminomethyl, aminoethyl, dimethylaminoethyl, carboxy, methoxycarbonyl and ethoxycarbonyl.

Examples of R when it is

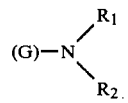

includes amino, methylamino, dimethylamino, hydroxyethylamino, dihydroxyethylamino, 1-piperidinyl, 1-pyridinium, N-morpholinyl, 1-pyrrolyl, 1-imidiazolyl, 1-pyridazinium and 1-pyrimidinium and R may also be a radical trimethylammonium as well as the quaternary ammonium derivatives of the said heterocyclics such as 1-pyridinium. R may also be (H) a halogen such as fluorine, chlorine, bromine or iodine, (I) optionally substituted 1,2-epoxy-ethyl or the resulting group with the epoxy groups opened with a nucleophile such as amines, sulfides, phenates, alcoholates or with a hydrogen halide such as hydrofluoric acid to obtain groups such as

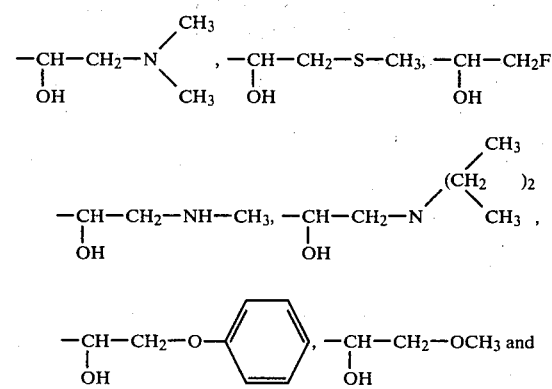

-continued $$-\underset{\underset{OH}{|}}{CH}-CH_2-O-CH_2-CH_3.$$

Examples of groups of B are selected from the same group as R discussed above when R is optionally substituted alkoxy, aryloxy or aralkoxy such as methoxy, ethoxy, propoxy, phenoxy, benzyloxy, etc.

Examples of R when it is (J) protected formyl are the groups of acetal type and especially 1,3-dioxolan-2-yl, dimethoxymethyl and diethoxymethyl. Examples of R when it is (K) —COOR' in the ester form are those wherein R' is alkyl of 1 to 7 carbon atoms such as methyl, ethyl, propyl, isopropyl and butyl or alkoxyalkyl such as methoxymethyl and isopropoxymethyl or alkylthioalkyl such as methylthiomethyl and isopropylthiomethyl or acyloxyalkyl such as pivaloyloxymethyl and acetoxyethyl. Examples of R' as a cation are the salts of sodium, potassium, lithium, calcium, magnesium, ammonium and non-toxic, pharmaceutically acceptable organic amines such as trimethylamine, diethylamine, triethylamine or tris-(hydroxymethyl)-aminomethane.

Among the acyl radicals there may be mentioned especially the acetyl, propionyl, butyryl, isobutyryl, n-valeryl, isovaleryl, tert-valeryl and pivalyl radicals.

Examples of R$_a$ are hydrogen and acyl of an aliphatic carboxylic acid, especially acids of 1 to 7 carbon atoms such as acrylic acid and alkanoic acids such as acetic acid, propionic acid, n-butyric acid, isobutyric acid, n-valeric acid, isovaleric acid and pivalic acid.

Examples of suitable acids for the non-toxic, pharmaceutically acceptable acid addition salts are mineral acids such as hydrochloric acid, hydrobromic acid, hydroiodic acid, sulfuric acid and phosphoric acid and organic acids such as acetic acid, propionic acid, trifluoroacetic acid, maleic acid, tartaric acid, methanesulfonic acid, benzenesulfonic acid, p-toluenesulfonic acid and preferably stearic acid, ethylsuccinic acid and laurylsulfuric acid.

Among the preferred compounds of formula I are those wherein R is selected from the group consisting of alkoxy, alkylthio, alkenyloxy, alkenylthio, alkynyloxy, alkynylthio, aryloxy, aralkoxy, arylthio or aralkylthio, the said groups optionally substituted with at least one member of the group consisting of halogen and alkoxy and alkylthio of 1 to 6 carbon atoms or R is

wherein R$_1$ and R$_2$ have the above definitions.

Among the especially preferred compounds of formula I are those wherein R is selected from the group consisting of halogen, dialkylamino, alkoxy optionally substituted with alkoxy or dialkylamino, aryloxy or aralkoxy optionally substituted with a halogen and alkylthio or aryl alkylthio optionally substituted with a halogen.

Especially preferred compounds of the invention are compounds of the formula

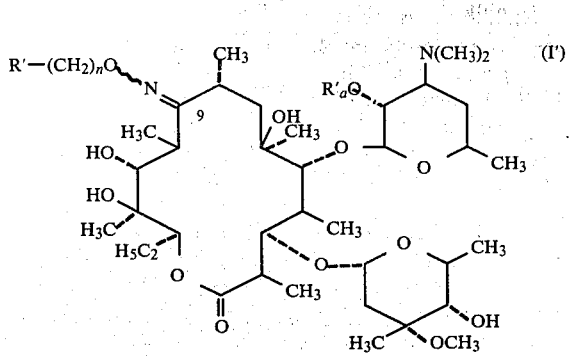
(I')

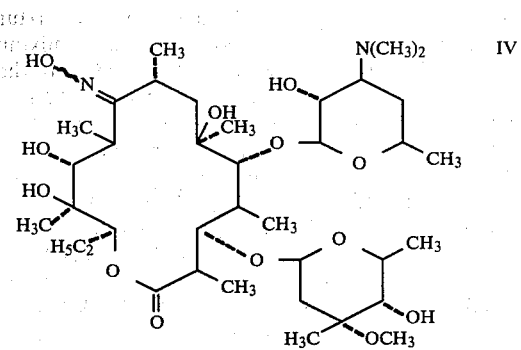
IV wherein n is an integer from 1 to 6, R' is selected from the group consisting of alkoxy and alkoxyalkoxy of 1 to 6 carbon atoms, phenoxy or benzyloxy optionally substituted with a chlorine and dialkylamino of 1 to 7 alkyl carbon atoms and $R_a'$ is selected from the group consisting of hydrogen and acyl of an alkanoic acid of 2 to 6 carbon atoms and their non-toxic, pharmaceutically acceptable acid addition salts. Especially preferred are the compounds wherein R' is $CH_3—(CH_2)_{n'}—O—$ where n' is an integer from 0 to 3 or $CH_3—(CH_2)_{n'}—O—(CH_2)_{n''}—O—$ wherein n' has the above definition and n" is an integer from 1 to 3 or

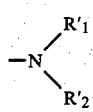

wherein $R_1'$ and $R_2'$ are alkyl of 1 to 3 carbon atoms.

Specific preferred compounds of the invention are 9-[0-({2-methoxyethoxy}methyl)-oxime] of erythromycin, 9-[0-(2-dimethylaminoethyl)-oxime] or erythromycin, 9-[0-(2-diethylaminoethyl)-oxime] of erythromycin and their non-toxic, pharmaceutically acceptable acid addition salts.

The novel process of the invention for the preparation of the compounds of formula I comprises either reacting in the optional presence of a base an erythromycin of the formula

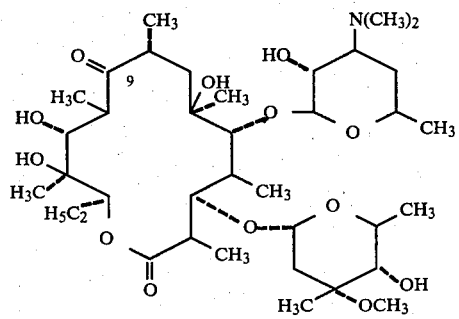
II with a compound of the formula $H_2N—O—A—R$      III wherein A and R have the above definitions or with a salt thereof with a strong acid to obtain a compound of formula $I_1$ which is a compound of formula I wherein $R_a$ is hydrogen or by reacting in the optional presence of a base a 9-oxime of erythromycin of the formula in the form of one of its isomers or a mixture thereof with a compound of the formula Hal—A—R      V wherein A and R have the above definition and Hal is a halogen to obtain a compound of formula $I_1$ and optionally when R is a halogen or alkoxy, alkenyloxy, alkynyloxy, alkylthio, alkenylthio or alkynylthio substituted with a halogen, reacting the said compound of formula $I_1$ with an amine of the formula

wherein $R_1'$ and $R_2'$ are individually selected from the group consisting of hydrogen and alkyl or 1 to 6 carbon atoms or taken together with the nitrogen to which they are attached form a heterocycle optionally containing a second heteroatom and optionally substituted to form the compound of formula $I_2$ which corresponds to a compound of formula I wherein $R_a$ is hydrogen and R is either

or alkoxy, alkenyloxy, alkynyloxy, alkylthio, alkenylthio or alkynylthio substituted with

or optionally when R is optionally substituted 1,2-ethoxyethyl, reacting the compound of formula $I_l$ with a nucleophilic reactant to obtain a compound of formula $I_3$ which corresponds to the compound of formula I wherein $R_a$ is hydrogen and R is a radical resulting from the opening of the epoxy group and the compounds of formula I wherein $R_a$ is hydrogen may be esterified to obtain the compounds of formula I wherein $R_a$ is acyl and optionally salifying the compounds of formula I.

In a preferred mode of the process of the invention, the compound of formula III is used in the form of its hydrohalide salts, especially the hydrobromide or hydrochloride and the reaction is preferably effected in a buffered media such as in the presence of an excess of an organic amine such as triethylamine or in a mixture of organic acid and a salt thereof such as a mixture of acetic acid and sodium acetate. Also useful are the use of alkali metal or alkaline earth metal carbonates or bicarbonates such as sodium carbonate, sodium bicarbonate, potassium carbonate, potassium bicarbonate, calcium carbonate or barium carbonate and the reaction is preferably effected in an alcoholic solvent such as methanol or ethanol, preferably anhydrous.

The reaction of the compounds of formulae IV and V is preferably effected in the presence of a base such as triethylamine or in the presence of an alkali metal or alkaline earth metal carbonate or bicarbonate as discussed above or in the presence of an alkali metal hydride such as sodium hydride. The reaction is preferably effected in a polar solvent such as acetone, dimethylformamide, dimethylsulfoxide or hexamethylphosphotriamide but equally useful is an ether such as ethyl ether, tetrahydrofuran or dioxane.

In both instances, the reaction temperature may vary from room temperature up to the reflux temperature of the solvent used and the reaction time may vary from several hours up to several days to obtain a complete reaction. The salification and the esterification reactions can be effected by the usual known methods.

A particularly preferred mode of the process of the invention for the preparation of a compound of formula I comprises reacting a compound of formula II with the hydrochloride or hydrobromide of the compound of formula III in the presence of an organic amine base or an alkaline earth metal carbonate or by reacting a compound of formula IV with a compound of formula V in the presence of a base selected from the group consisting of sodium carbonate, sodium bicarbonate, potassium carbonate, potassium bicarbonate, calcium carbonate, barium carbonate and sodium hydride.

The novel antibiotic compositions of the invention are comprised of an antibiotically effective amount of at least one compound selected from the compounds of formula I and their non-toxic, pharmaceutically acceptable acid addition salts and an inert pharmaceutical carrier or excipient. The compositions may be in the form of tablets, dragees, gelules, granules, suppositories, injectable solutions or suspensions, pomades, creams or gels or a powder for dissolution in an appropriate vehicle just before use such as sterile pyrogen water.

Examples of suitable excipients are talc, arabic gum, lactose, starch, magnesium stearate, cacao butter, aqueous or non-aqueous vehicles, fatty bodies of animal or vegetable origin, paraffinic derivatives, glycols, diverse wetting agents, dispersants or emulsifiers and preservatives.

The compositions of the invention possess a very good antibiotic activity against gram positive bacteria such as staphylococcus, streptococcus and pneumococcus. The compositions are useful for the treatment of infections of sensitive germs and especially of staphylococcia such as staphylococcia septicemia, malignic staphyloccia of the face or skin, pyodermitis, septic or suppurantic sores, boils, anthrax, phlegms, eresipeles, pulmonary supporations, primitive acute or post grip staphylococcia, bronchopneumonia; streptococcia such as acute angina, otitis, sinusitus, scarlatin; pneumococcia such as pneumonia, bronchitis; brucellosis, diphtheria and gonococcia. The compositions are also useful against infections caused by germs such as Haemophilus influenza, Haemophilus Pertussis, Rickettsis and Mycoplasma pneumonia.

Among the preferred compositions of the invention are those wherein the active ingredient is selected from the group consisting of 9-[0-({2-methoxyethoxy}-methyl)-oxime] of erythromycin, 9-[0-(2-dimethylaminoethyl)-oxime] of erythromycin, 9-[0-(2-diethylaminoethyl)-oxime] of ethythromycin and their non-toxic, pharmaceutically acceptable acid additions salts.

The novel method of the invention for combatting bacterial infections in warm-blooded animals, including humans, comprises administering to warm-blooded animals an antibiotically effective amount of at least one compound of formula I and their non-toxic, pharmaceutically acceptable acid addition salts. The active compounds may be administered orally, rectally, parenterally or topically to the skin or mucous, preferably orally. The active daily dose will vary depending upon the specific compound, the complaint treated, the person concerned and method of administration. For example, the compounds of Examples 1 or 5 may be orally administered daily at a dose of 5 to 80 mg/kg.

In vitro, the compounds of the invention have properties similar to those of erythromycin but in vivo, the compounds of the invention have two very interesting advantages: first, the protection of animals infected experimentally is realized at lower doses than erythromycin or erythromycin propionate and second, the pharmacological results show a clear superiority as compared to erythromycin.

The starting compounds of formula III may be prepared by the process generally described in Angew. Chem., Vol. 68 (1956), No. 8., page 303 and the oxime of erythromycin is described in British Pat. No. 1,100,504. The compounds of formula V are known or can be prepared by known processes.

Among the preferred compounds of formula I are those wherein $R_a$ is hydrogen and A and R have the values set forth in Table I.

TABLE I

| A | B |
|---|---|
| $-CH_2-$ | $CH_3-(CH_2)_3-O-$ |
| $-CH_2-$ | $iPr-O-$ |
| $-CH_2-$ | $-CH(OH)-CH_2-S-CH_3$ |
| $-CH_2-$ | $-CH(OH)-CH_2-NHCH_3$ |
| $-(CH_2)_2-$ | $CH_3-O-$ |
| $-(CH_2)_2-$ | $Br$ |
| $-(CH_2)_3-$ | $Et\diagdown N-/H$ |
| $-(CH_2)_3-$ | $iPr\diagdown N-/iPr$ |
| $-(CH_2)_2-$ | $-NH\,CH_3$ |
| $-(CH_2)_2-$ | $nPr\diagdown N-/H$ |

TABLE I-continued

| A | B |
| --- | --- |
| —(CH$_2$)$_3$— | H$_2$N— |

Besides the derivatives of erythromycin A of the present invention, it is evident that within the scope of the invention are the corresponding oxime derivatives of erythromycin B wherein the 12-hydroxyl group is replaced by hydrogen and of erythromycin C wherein the 3"-methoxy group is replaced with a hydroxyl.

In the following examples there are described several preferred embodiments to illustrate the invention. However, it should be understood that the invention is not intended to be limited to the specific embodiments.

EXAMPLE 1

9-[0-(2-methoxyethoxy)-methyloxime] of erythromycin

A mixture of 1.87 g of the oxime of erythromycin, 25 ml of acetone, 0.94 g of sodium bicarbonate and 0.3 ml of (methoxyethoxy)-methyl chloride was refluxed under an inert atmosphere for 16 hours during which another 0.3 ml of (methoxyethoxy)-methyl chloride were added once. The mixture was vacuum filtered and the filtrate was concentrated to ⅓ of its volume. An aqueous sodium bicarbonate solution was added to the mixture which was then extracted with ether. The organic phase was dried and evaporated to dryness and the residue was chromatographed over silica gel. Elution with a 15-1 benzene-triethylamine mixture yielded 1.29 g of 9-[0-(2-methoxyethoxy)methyloxime] of erythromycin with a specific rotation of $[\alpha]_D^{20} = -77.5° \pm 2°$ (c=0.45% in chloroform) and an Rf=0.2 (silica support 9-1 benzene-triethylamine eluant).

Analysis: C$_{41}$H$_{76}$N$_2$O$_{15}$; molecular weight=837; Calculated: %C, 58.8; %H, 9.16; %N, 3.35. Found: %C, 59; %H, 9.20; %N, 3.30.

EXAMPLE 2

9-[0-(2-{4-chlorophenoxy}-ethyl)-oxime] of erythromycin 18.5 ml of methanolic 3.25 N hydrogen chloride in methanol were added to a solution of 11.4 g of (4-chlorophenoxy)-2-ethoxyamine in 230 ml of anhydrous methanol and the mixture was stirred at room temperature for 30 minutes. A mixture of 21 g of erythromycin, 11 g of barium carbonate and 35 ml of methanol were added to the mixture which was then stirred at room temperature for 18 hours and was filtered. The filtrate was poured into 750 ml of water containing 75 ml of concentrated ammonium hydroxide and the mixture was extracted with chloroform. The organic phase was washed with a 10% ammonium hydroxide solution, dried and evaporated to dryness to obtain 35 g of a resin. The latter was chromatographed over silica gel and was eluated with a 9-1 chloroform-triethylamine mixture to obtain 1.925 g of 9-[0-(2-{4-chlorophenoxy}-ethyl)-oxime] of erythromycin and 2.03 g of an impure product. The latter was chromatographed over silica gel and was eluted with a 15-1 benzene-triethylamine mixture to obtain another 1.42 g of 9-[0-(2-{4-chlorophenoxy}-ethyl)-oxime] of erythromycin having a specific rotation of $[\alpha]_D^{20} = -79.5° \pm 2.5°$ (c=1% in ethanol).

EXAMPLE 3

9-[0-(2-ethoxyethyl)-oxime] of erythromycin 1.4 ml of triethylamine and then 2.8 g of 0-(2-ethoxyethyl)-hydroxylamine hydrochloride were added to a solution of 3.7 g of erythromycin in 25 ml of dry methanol and the mixture was stirred under an inert atmosphere at room temperature for 96 hours. The mixture was poured into a mixture of 12 ml of 28% ammonium hydroxide in 50 ml of water and the mixture was cooled in an ice-water bath. The mixture was filtered and the recovered product was washed with water and taken up in methylene chloride. The organic phase was washed with aqueous saturated sodium chloride solution, dried and evaporated to dryness to obtain 3.83 g of raw product. The latter was chromatographed over silica gel and was eluted with a 15-1 benzene-triethylamine mixture to obtain 1.9 g of 9-[0-(2-ethoxyethyl)-oxime] of erythromycin with a specific rotation of $[\alpha]_D^{20} = -73° \pm 3°$ (c=0.6% in CHCl$_3$).

EXAMPLE 4

9-[0-(2-ethoxyethoxymethyl)-oxime] of erythromycin 1 g of sodium bicarbonate was added to a solution of 1.89 g of the oxime of erythromycin in 25 ml of acetone and then 0.36 ml of 1-(chloromethoxy)-2-ethoxy-ethane was added thereto. The mixture was stirred at room temperature for 24 hours and was then refluxed for 75 hours while adding once 0.2 ml and a second time 0.15 ml of 1-(chloromethoxy)-2-ethoxy-ethane. The mixture was filtered and the filtrate was poured into 100 ml of water. The mixture was extracted with ether and the organic phase was dried and evaporated to dryness under reduced pressure to obtain 2.5 g of residue. The latter was chromatographed over silica gel and was eluted with a 9-1 benzene-triethylamine mixture to obtain 1.72 g of 9-[0-(2-ethoxyethoxymethyl)-oxime] of erythromycin with a specific rotation of $[\alpha]_D^{20} = -79° \pm 2°$ (c=0.7% in ethanol).

EXAMPLE 5

9-[0-(2-dimethylaminoethyl)-oxime] of erythromycin 6.3 g of sodium bicarbonate and 1.65 g of 2-dimethylamino-1-chloro-ethane hydrochloride were added to a solution of 5.6 g of the oxime of erythromycin in 80 ml of acetone and the mixture refluxed for 4½ days while adding thereto 4 times 3.3 g of 2-dimethylamino-1-chloro-ethane hydrochloride. The mixture was filtered and the filtrate was concentrated to cause precipitation of 4.5 g of product. The mixture was filtered and the filtrate was poured into 100 ml of water. The mixture was extracted with ether and the organic phase was washed with aqueous saturated sodium chloride solution, was dried and evaporated to dryness. The residue and the 4.5 g of product were chromatographed over silica gel and were eluted with a 100-15 chloroform-triethylamine mixture to obtain 4.38 g of 9-[0-(2-dimethylaminoethyl)-oxime] of erythromycin with a specific rotation of $[\alpha]_D^{20} = -99.5° \pm 2°$ (c=1% in ethanol).

EXAMPLE 6

9-[0-(2-methoxyethoxymethyl)-oxime] of erythromycin 56 g of dry sodium bicarbonate and 15.2 ml of (methoxyethoxy)methyl chloride were added to a solution of of 99.6 g of the oxime of erythromycin in 1000 ml of dry acetone and the mixture was refluxed with stirring under a nitrogen atmosphere for 15 hours. 7.6 ml of (methoxyethoxy)-methyl chloride were added to the mixture which was refluxed for 8 hours followed by a third addition of 5 ml of the said chloride and 15 hours of reflux. The mixture was cooled and filtered and the filter was rinsed with acetone. The filtrate was evaporated to dryness and the resin residue was triturated with 500 ml of a concentrated sodium bicarbonate solution. The mixture was filtered and the amorphous product was rinsed with water and dried in an oven and the procedure was repeated three times to obtain 335.6 g of raw product which was substantially a quantitative yield.

The said product was dissolved in 1.5 liters of pure acetone and 15 g of activated carbon and 15 g of Kieselguhr were added thereto. The mixture was stirred for a few minutes and was then filtered. The product was rinsed and washed with 300 ml of acetone and the treatment was repeated with 3 g of activated carbon and 15 g of Kieselguhr. After filtration, the filter was washed and rinsed with 300 ml of acetone and the filtrate was evaporated to 1.5 liter under reduced pressure. 800 ml of distilled water were added to the hot solution and crystallization was induced. The mixture was allowed to stand at 20°–25° C. for crystallization until it became a mass before cooling to 0° to 5° C. The crystals were filtered and were washed with acetone containing 40% iced water to obtain a first yield of 134.5 g and a second yield of 75.9 g and a third yield of 15.3 g for a total yield of 225.7 g of 9-[0-(2-methoxyethoxymethyl)-oxime] of erythromycin.

The product was dissolved in 645 ml of acetone and 215 g crystallized therefrom. 5 g of Kieselguhr were added thereto and the mixture was stirred for a few minutes and filtered to obtain a slightly colored, limpid solution. 525 ml of distilled water were added portion wise thereto and crystallization was induced by scratching and seeding. The mixture stood at 20°–25° C. for crystallization to develope and after 2 hours, it became a mass. The mixture stood at 0° to 5° C. overnight and was filtered. The crystals were rinsed and washed with 100 ml of acetone containing 40% of water and dried at 40° C. under reduced pressure to obtain 170 g of product. A second and third yield of 16 and 9.5 g, respectively were obtained for a total yield of 195.5 g of pure 9-[0-(2-methoxyethoxmethyl)-oxime] of erythromycin.

EXAMPLE 7

9-[0-benzyloxymethoxy-oxime] of erythromycin 1.2 g of sodium bicarbonate and 0.53 ml of benzyl chloromethyl ether were added to a solution of 1.9 g of the oxime of erythromycin in 25 ml of acetone and the mixture was stirred under nitrogen at room temperature for one hour. The suspension in acetone was refluxed at 60° C. for 25 hours and 0.25 ml of benzyl chloromethyl ether were added thereto. The mixture was refluxed for another 41½ hours after which another 0.25 ml of the said ether were added. The mixture was refluxed for 45 hours and was then filtered. The filter was rinsed with acetone and the filtrate was poured into 100 ml of water to obtain a milky solution. The solution was extracted 3 times with 200 ml of ether and the combined ether phases were washed with aqueous saturated sodium chloride solution, was dried and evaporated to dryness under reduced pressure. The 3.4 g of resin residue were chromatographed over silica gel and was eluted with a 9-1 benzene-triethylamine mixture to obtain 1.2 g of purified product.

The latter was dissolved in 20 ml of acetone and the mixture was concentrated to a volume of 2 ml. The cold mixture was taken up in 60 ml of petroleum ether (b.p.=64°–75° C.) and the mixture was filtered. The crystals were washed with petroleum ether to obtain 0.715 g of product. The latter was dissolved in 100 ml of acetone and the solution was stirred with activated carbon at 50° C. for 10 minutes and was filtered hot. The acetone solution was concentrated to a volume of 2 ml and was then taken up in 100 ml of petroleum ether (b.p.=64°–75° C.). Crystallization occured and the mixture was filtered. The crystals were rinsed with petroleum ether and was dried under reduced pressure at 60° C. to obtain 0.585 g of pure 9-[0-benzyloxymethoxy-oxime] of erythromycin with a specific rotation of $[\alpha]_D^{20} = -74.5° \pm 3°$ (c=0.25% in ethanol).

Analysis: $C_{45}H_{76}N_2O_{14}$; molecular weight=869.1; Calculated: %C, 62.19; %H, 8.81; %N, 3.22. Found: %C, 62.1; %H, 8.8; %N, 3.1.

EXAMPLE 8

9-[0-{2-(dimethylamino)ethyl}-oxime] of erythromycin 3.6 g of sodium carbonate and then 3.24 g of dimethylaminochloroethane hydrochloride were added to a solution of 11.2 g of the oxime of erythromycin in 160 ml of acetone and the mixture was refluxed with stirring for 93 hours and was then cooled. The mixture was filtered and the filter was rinsed with acetone. The filtrate was evaporated under reduced pressure to a volume of 150 ml when crystallization occured. The mixture was cooled to 5° C. and was filtered. The crystals were rinsed to obtain 2.45 g of crystals designated as product A.

The insolubles were taken up in 200 ml of acetone and the mixture was stirred for 30 minutes and was filtered. The acetone was evaporated in 2 steps and 0.864 g of product B crystallized. The operation was repeated several times to obtain 3.37 g of product C. The new insolubles were taken up in about 200 ml of acetone and the mixture was heated at 50° C. with stirring for 30 minutes. The mixture was filtered hot and the acetone was evaporated in 2 steps. The mixture was cooled and filtered and the crystals were rinsed with cold acetone and dried to obtain 2.64 g of product D. Another 0.661 g of product were obtained from the mother liquors of product A for a total yield of 9.989 g of product. The 9.989 g were dissolved in 800 ml of acetone containing 1 g of activated carbon and the mixture was stirred at 50° C. for 15 minutes and was filtered. The colorless, limpid filtrate was concentrated to about 250 ml for crystallization and the mixture was cooled and filtered. The crystals were washed and dried to obtain a first yield of 8.27 g and a second yield of 0.714 g of 9-[0-{2-dimethylamino}ethyl)-oxime] of erythromycin with a specific rotation of $[\alpha]_D^{20} = -86° \pm 2°$ (c=1% in chloroform). The product was identical to that of Example 5.

EXAMPLE 9

9-[0-{(2-dimethylamino)-ethyl}-oxime] of erythromycin 0.159 g of sodium hydride ws a 50% suspension in oil was added under argon portion-wise to a mixture of 40 ml of a 3-1 hexamethylphosphotriamide-ether mixture and 2.247 g of the oxime of erythromycin and the mixture was stirred for 15 minutes. A solution of 21 ml of hexamethylphosphotriamide, 0.518 of 2-dimethylaminoethyl chloride hydrochloride and 0.173 g of sodium hydride was added dropwise to the mixture and the mixture was stirred for 20 minutes. The reaction was complete after 4 hours and the mixture was poured into 30 ml of water saturated with 60 g of ammonium acetate. The mixture was extracted with ether and the organic phase was washed with water and dried and evaporated to dryness. The residue was diluted with water and the solution was extracted with toluene. The organic phase was dried and evaporated to dryness under reduced pressure. The residue was taken up in a minimum of pentane and crystallization was induced by seeding. The mixture was stirred at room temperature for 3 hours and was vacuum filtered. The crystals were dried at 60° C. to obtain 0.21 g of 9-[0{-(2-dimethylamino)-ethyl}-oxime] of erythromycin melting at 233° C. The differetn mother liquors were further treated. The product was identical to the compounds of Examples 5 and 8.

EXAMPLE 10

9-[0-(2-{dimethylamino}-ethyl)-oxime] of erythromycin

Using the procedure of 9, 53 mg of sodium hydride was added in 2 portions to a mixture of 0.75 g of the oxime of erythromycin in 3.5 ml of dimethylformamide and the mixture was stirred for 15 minutes. 0.158 g of 2-dimethylamino-ethyl chloride hydrochloride and 53 mg of sodium hydride in 2 portions were added to the mixture and after 4 hours at room temperature, 29 mg of 2-dimethylaminoethyl chloride hydrochloride and 11 mg of sodium hydride in 2 portions was added to the mixture. The mixture was stirred overnight and was saturated with carbon dioxide. The mixture was poured into 35 ml of water and the mixture was vacuum filtered. The filter was rinsed and the product was taken up in chloroform. The organic phase was dried and evaporated to dryness and the residue was crystallized from 2 ml of pentane to obtain 0.428 g of 9-[0-(2-{dimethylamino}-ethyl)-oxime] of erythromycin. The mother liquors were treated to obtain a second yield of 210 mg of the said product which was identical to the product of Examples 5, 8 and 9.

EXAMPLE 11

9-[0-({4-chlorophenoxy}-methyl)-oxime] of erythromycin 0.159 g of sodium hydride as a 50% suspension in oil was added portion-wise to a mixture of 2.247 g of the oxime of erythromycin in 60 ml of ether and the mixture was stirred for 15 minutes. Then, 6 ml of hexamethylphosphotriamide were added to the mixture after which a solution of 6 ml of 0.45 ml of p-chloroanisole chloride in ether was added thereto dropwise over 15 minutes. The reaction was complete in 40 minutes and the mixture was then poured into 30 ml of water saturated with 60 g of ammonium acetate. The mixture was extracted 3 times with 15 ml of ether and the combined ether phases were washed with water after which a precipitate appeared. Ethyl acetate was added until total dissolution occured and the decanted organic phase was washed with water and then with an aqueous saturated sodium chloride solution, was dried and evaporated to dryness. The residue was taken up in pentane and the mixture was stirred at room temperature for 16 hours and was vacuum filtered. The product was rinsed with pentane and dried to obtain 1.99 g of product.

1.89 g of the said product and 3.8 g of activated magnesium silicate in 40 ml of benzene were stirred for one hour and the mixture was vacuum filtered. The filter was rinsed with 5 ml of benzene and the filtrate was evaporated to dryness. The operation was repeated once and the residue was then taken up in 5 ml of pentane. The mixture was stirred overnight at room temperature and was vacuum filtered. The product was rinsed with 0.5 ml of pentane and dried to obtain 0.903 g of 9-[0-({4-chlorophenoxy)-methyl)-oxime] of erythromycin melting at 90° C. and having a specific rotation of $[\alpha]_D^{20} = -64.5° \pm 2.5°$ (c=0.5% in ethanol).

NMR Spectrum (deuterochloroform)

Peaks at 2.27 ppm (dimethylamio); at 5.65 ppm (d,d 7 hz) (—N OCH$_2$O).

Analysis: Calculated: %C, 59.41; %H, 8.27; %N, 3.15; %Cl, 3.98. Found: %C, 59.5; %H, 8.4; %N, 3.0; %Cl, 4.0.

EXAMPLE 12

9-[0-(cyanomethyl)-oxime] of erythromycin 0.21 g of sodium hydride as a 50% oil suspension were added portion-wise under argon to a mixture of 3 g of the oxime of erythromycin and 80 ml of acetone and the mixture was stirred for 15 minutes. A solution of 0.384 g of acetonitrile chloride in 1 ml of acetone was added to the mixture and 20 minutes later, 0.141 g of sodium hydride was added thereto. 10 minutes later, 0.256 g of acetonitrile chloride were added to the mixture followed 10 minutes later by the addition of 70 mg of sodium hydride and 0.125 g of acetonitrile chloride. The mixture was saturated with carbon dioxide for 90 minutes and was then evaporated to dryness under reduced pressure. The residue was dried, chromatographed over silica gel and was eluted with an 85-15 ether-triethylamine mixture. The collected fractions were evaporated to dryness and the residue was crystallized from petroleum ether (b.p.=65°-75° C.). The mixture was vacuum filtered and the recovered product was washed and dried to obtain 1.8 g of 9-[0-(cyanomethyl)-oxime] of erythromycin melting at 140° C. and having a specific rotation of $[\alpha]_D^{20} = -74.5° \pm 2.5°$ (c=0.6% in chloroform).

Analysis: Calculatd: %C, 59.45; %H, 8.83; %N, 5.33. Found: %C, 59.2; %H, 9.0; %N, 5.0.

EXAMPLE 13

9-[0-(2-ethylthioethyl)-oxime] of erythromycin

A mixture of 90 ml of methyl ethyl ketone, 10 ml of 2-chloroethylethyl sulfide and 12.9 g of sodium iodide under argon was refluxed for one hour and was cooled and vacuum filtered to remove the sodium chloride formed. The filtrate was saved in a hermetically sealed flask.

3.75 g of oxime of erythromycin were added under argon to 24 ml of a 1-1 hexamethylphosphotriamide-ether solution and the ether was evaporated under reduced pressure. Then, 0.26 g of sodium hydride as a 50% oil suspension were added thereto and the mixture was stirred for 15 minutes. Then, 50 ml of the first solution were added to the mixture over 20 minutes and 0.6 g of sodium hydride were added thereto portion-wise. After 50 minutes, another 0.59 g of sodium hydride were added thereto and after one hour, the mixture was poured into 240 ml of an aqueous three-fourths saturated sodium chloride solution containing 10 g of sodium bicarbonate. The mixture was stirred at room temperature for 10 minutes and was then vacuum filtered. The product was dissolved in chloroform and the solution was dried and evaporated to dryness. The 5 g of liquid were chromatographed over silica gel and were eluted with a 9-1 toluene-triethylamine mixture. The combined homogenous fractions were evaporated to dryness to obtain 1.1 g of resin which was triturated with petroleum either (b.p.=65°-75° C.) and dried to obtain 1.036 g of 9-[0-(2-ethylthio-ethyl)-oxime] of erythromycin melting at 110° C. and having a specific rotation of $[\alpha]_D^{20} = 72.5° \pm 2°$ (c=1% in chloroform).

Analysis: Calculated: %C, 58.83; %H, 9.15; %N, 3.35; %S, 3.83. Found: %C, 58.8; %H, 9.3; %N, 3.3; %S, 3.7.

EXAMPLE 14

9-[0-(2-cyanoethyl)-oxime] of erythromycin 0.2 g of sodium hydride as a 50% oil suspension and 0.4 ml of purified bromopropionitrile (dropwise) were added under argon to a solution of 10 ml of hexamethylphosphotriamide and 3 g of the oxime of erythromycin and after 45 minutes, another 0.1 g of sodium hydride and 4 drops of bromopropionitrile were added thereto. After 45 minutes, another 0.7 g of sodium hydride and 0.42 ml of bromopropionitrile were added thereto and the mixture was poured into 240 ml of aqueous three-fourths saturated sodium chloride solution containing 2.4 g of sodium bicarbonate. The mixture was stirred for one hour and was vacuum filtered and the filter was rinsed with aqueous saturated sodium chloride solution. The product was dissolved in 200 ml of chloroform and the mixture was stirred for one hour and was vacuum filtered. The filter was washed with chloroform and the combined filtrate and wash waters were decanted. The chloroform phase was dried, filtered and evaporated to dryness under reduced pressure to obtain 3.26 g of raw product in the form of an amorphous powder. 2 g of the latter product were chromatographed over silica gel and were eluted with a 95-5 chloroform-triethylamine mixture. The homogeneous fraction of 1.348 g of resin was taken up in pentane and the mixture was stirred for 16 hours and was then evaporated to dryness under reduced pressure. The residue was taken up in 10 ml of pentene and the solution was stirred for 30 minutes and was then vacuum filtered. The recovered product was rinsed and dried to obtain 0.766 g of 9-[0-(2-cyanoethyl)-oxime] of erythromycin in the form of white crystals melting at 210° C. and having a specific rotation of $[\alpha]_D^{20} = -77.5° \pm 1.5°$ (c=1% of chloroform).

Analysis: Calculated: %C, 59.9; %H, 8.92; %N, 5.24. Found: %C, 59.6; %H, 9.0; %N, 5.5.

EXAMPLE 15

9-[0-(3,3-dimethyl-2-oxo-butyl)-oxime] of erythromycin 3 g of oxime of erythromycin were added portionwise under argon to 10 ml of hexamethylphosphotriamide and 0.22 g of sodium hydride as a 50% oil suspension were added thereto. The mixture was cooled to 10° C. and 0.6 ml of 3,3-dimethyl-2-oxo-butyl bromide were added dropwise thereto. The mixture was held at 10° to 12° C. for 25 minutes and was then slowly poured into 200 ml of an aqueous three-fourths saturated sodium chloride solution containing 1.6 g of sodium bicarbonate. The mixture was rinsed with an aqueous three-fourths saturated sodium chloride solution, was stirred for 20 minutes and was then vacuum filtered. The recovered product was dissolved in chloroform and the decanted organic phase was washed, dried and evaporated to dryness under reduced pressure. The 3.28 g of residue was combined with 5.1 g of product prepared in the same manner and the material was chromatographed over silica gel. Elution with a 6-4-1 toluene-chloroform-triethylamine mixture yielded a homogenous fraction which was evaporated to dryness under reduced pressure. The residue was dissolved in pentane and the solution was agitated and evaporated to dryness. The residue was stirred in 3 ml of pentane and the mixture was vacuum filtered. The material was rinsed with 0.3 ml of pentane and was dried to a constant weight to obtain 0.67 g of 9-[0-(3,3-dimethyl-2-oxo-butyl)-oxime] of erythromycin in the form of a white powder melting at 146° C. and having a specific rotation of $[\alpha]_D^{20} = -63.5° \pm 1.5°$ (c=1% in chloroform).

Analysis: Calculated: %C, 60.97; %H, 9.28; %N, 3.31. Found: %C, 60.8; %H, 9.3; %N, 3.2.

EXAMPLE 16

9-[0-(3-ethylthio-2-hydroxy-propyl)-oxime] of erythromycin

A mixture of 5 g of the oxime of erythromycin and 34 ml of a 1-1 mixture of ether-hexamethylphosphotriamide was heated under reduced pressure to distill the ether and then 0.352 g of sodium hydride as a 50% oil suspension were added thereto portion-wise under argon. The mixture was stirred for 15 minutes and then 1.25 g of 3-ethylthio-2-hydroxy-propyl chloride were added thereto. After 15 minutes, another 0.352 g of sodium hydride were added to the mixture and when the reaction was complete as determined by thin layer chromatography, the mixture was poured into 400 ml of aqueous three-fourths saturated sodium chloride solution containing 1.7 g of sodium bicarbonate. The mixture was vacuum filtered and the product was dissolved in chloroform. The solution was dried and evaporated to dryness under reduced pressure to obtain 3.6 g of resin which was combined with 3.7 g of resin from another experiment. The product was chromatographed over silica gel and was eluted with a 9-1 chloroform-triethylamine mixture. The combined homogenous fractions were evaporated to dryness and the 2.7 g of white resin were chromatographed over silica gel. The product was eluted with a 1-1 chloroform-methanol mixture and the combined fractions were evaporated to dryness. The 1.116 g of white resin was crystallized with stirring from 20 ml of pentane and the mixture was vacuum filtered. The product was rinsed with pentane and dried to a constant weight to obtain 0.93 g of 9-[0-(3-ethylthio-2-hydroxy-propyl)-oxime] of erythromycin melting at 142° C. and having a specific rotation of $[\alpha]_D^{20} = -76.5° \pm 2.5°$ (c=0.8% in chloroform).

Analysis: Calculated: %C, 58.17; %H, 9.07; %N, 3.23; %S, 3.7. Found: %C, 58.0; %H, 9.1; %N, 3.2; %S, 3.6.

EXAMPLE 17

9-[0-(2-{2-hydroxyethoxy}-ethyl)-oxime] of erythromycin

A mixture of 3 g of oxime of erythromycin in 10 ml of hexamethylphosphotriamide was stirred under argon for 25 minutes and then 0.212 g of sodium hydride as a 50% oil suspension was added thereto. After stirring for 15 minutes, another 0.212 g of sodium hydride were added thereto followed by 0.6 g of 2-(2-chloroethoxy)-ethanol. The mixture was stirred for 15 minutes and then 0.212 g of sodium hydride and 0.6 g of 2-(2-chloroethoxy)-ethanol were added. After one hour, the reaction was complete and the mixture was slowly poured into 240 ml of aqueous three-fourths saturated sodium chloride solution containing 3 g of sodium bicarbonate. The mixture was stirred for 10 minutes and was vacuum filtered and the product was dissolved in chloroform. The solution was washed with aqueous saturated sodium chloride solution, was dried and evaporated to dryness under reduced pressure. The 3.5 g of resin were chromatographed over silica gel and were eluted with a 9-1 toluene-triethylamine mixture. The homogenous fractions were evaporated to dryness and the 2.9 g of resin were chromatographed over silica gel. Elution effected with a 12.7-7.5 chloroform-triethylamine mixture yielded 1.8 g of product. 1.063 g of the said product were triturated and then decanted 3 times with 5 ml of an aqueous saturated sodium chloride solution and the mixture was vacuum filtered. The product was washed with aqueous half-saturated sodium chloride solution, then with water and dried to obtain 0.718 g of 9-[0-(2-{2-hydroxyethyl}-ethyl)-oxime] of erythromycin as a white powder melting at 132° C. and having a specific rotation of $[\alpha]_D^{20} = -83.5° \pm 2°$ (c=1% in chloroform).

Analysis: Calculated: %C, 58.83; %H, 9.15; %N, 3.35. Found: %C, 59.0; %H, 8.9; %N, 3.2.

EXAMPLE 18

9-[0-{(4-chlorophenylthio)-methyl}-oxime] of erythromycin 0.212 g of sodium hydride as a 50% suspension in oil and then 8 ml of hexamethylphosphotriamide and 0.6 ml of 4-chlorophenylthio-methyl chloride were added with stirring under argon to a solution of 2.99 g of the oxime of erythromycin in 80 ml of ether and after 65 hours, another 0.15 ml of 4-chlorophenylthio-methyl chloride were added to the mixture. The mixture was stirred for 4 hours and was then poured into a solution of 100 g of amyl acetate in 60 ml of water. The mixture was extracted with ether and the organic phase was washed with water, dried and evaporated to dryness under reduced pressure. The 3 g of resin were chromatographed over silica gel and was eluted with a 9-1 toluene-triethylamine mixture. The combined fractions were evaporated to dryness at room temperature to obtain 0.89 g of an amorphous solid and 0.852 g of the product were stirred with 13 ml of pentane for 2 hours. The mixture was vacuum filtered and the product was washed 3 times with pentane and dried to obtain 0.753 g of 9-[0-{(4-chlorophenylthio)-methyl}-oxime] of erythromycin in the form of a white powder melting at 126° C. and having a specific rotation of $[\alpha]_D^{20} = -32.5° \pm 1.5°$ (c=0.8% in chloroform).

Analysis: Calculated: %C, 58.36; %H, 8.13; %N, 3.093; %S, 3.54; %Cl, 3.91. Found: %C, 58.6; %H, 8.1; %N, 3.0; %S, 3.7; %Cl, 4.2.

EXAMPLE 19

9-[0-(2-{1,1-dimethylethoxy}-2-oxo-ethyl)-oxime] of erythromycin 0.216 g of sodium hydride as a 50% oil suspension was added in small amounts with stirring to a solution of 3 g of the oxime of erythromycin in 80 ml of dry ether in a bath at 10° C. and after 8 minutes, 0.6 ml of tert.-butyl chloroacetate was added thereto dropwise. The temperature was returned to room temperature and 8 ml of anhydrous dimethylformamide were added to the mixture. After 2 hours, 0.044 g of sodium hydride and 0.12 ml of tert.-butyl chloroacetate were added to the mixture and after one hour, carbon dioxide was bubbled through the mixture until it was neutral. The mixture was vacuum filtered and the filtrate was evaporated to dryness. The residue was poured with stirring into 160 ml of aqueous concentrated sodium chloride solution and the mixture was stirred for one hour and was then vacuum filtered. The recovered product was washed with aqueous saturated sodium chloride solution and was dried under reduced pressure to obtain 3.85 g of a white solid.

3.7 g of the said product were chromatographed over silica gel and was eluted with a 9-1 toluene-triethylamine mixture and the homogenous fractions were evaporated to dryness. The amorphous residue was triturated with pentane and the mixture was evaporated to dryness under reduced pressure to obtain 1.73 g of a white powder melting at 214° C. The latter was empasted with 5.1 ml of pentane and the mixture was vacuum filtered. The product was washed twice with pentane and dried under reduced pressure to obtain 1.599 g of 9-[0-(2-{1,1-dimethylethoxy}-2-oxo-ethyl)-oxime] of erythromycin in the form of a white powder melting at 214° C. and having a specific rotation of $[\alpha]_D^{20} = -71.5° \pm 2°$ (c=1% in chloroform).

Analysis: Calculated: %C, 59.84; %H, 9.11; %N, 3.23. Found: %C, 60.1; %H, 9.4; %N, 3.1.

EXAMPLE 20

9-[0-(ethoxymethyl)-oxime] of erythromycin

A mixture of 3 g of the oxime of erythromycin in 10 ml of hexamethylphosphotriamide was rinsed with 2 ml of hexamethylphosphotriamide and after dissolution occured, 0.22 g of sodium hydride as a 50% oil suspension was added in 3 fractions thereto. 0.41 ml of chloromethyl ethyl ether were added with stirring under reduced pressure and the mixture was allowed to stand for 2 hours and was then poured into 250 ml of an aqueous three-fourths saturated sodium chloride solution containing 2 g of sodium bicarbonate. The mixture was rinsed with 20 ml of aqueous three-fourths saturated sodium chloride solution and was stirred for 30 minutes and then let stand. The mixture was vacuum filtered. The product was rinsed with the said sodium chloride solution and was then dissolved in chloroform. The decanted organic phase was vacuum filtered and the filtrate was washed, dried, treated with 0.8 g of activated carbon and was then evaporated to dryness under reduced pressure. The 3.01 g of yellow resin were chromatographed over silica gel and was eluted with a 6-4-1 toluene-chloroform-triethylamine mixture. The combined homogenous phases were evaporated to dryness under reduced pressure and the 2 g of white resin were solidified by trituration with 3 ml of isopropyl ether for 20 minutes. The mixture was vacuum filtered and the recovered product was rinsed and dried to obtain 1.54 g of 9-[0-(ethoxymethyl)-oxime] of erythromycin in the form of a white powder melting at 123° C. and having a specific rotation of $[\alpha]_D^{20} = -78° \pm 2.5°$ (c=1% in chloroform).

Analysis: Calculated: %C, 59.53; %H, 9.01; %N, 3.48. Found: %C, 59.8; %H, 9.3; %N, 3.3.

EXAMPLE 21

9-[0-{(2-chloroethoxy)-methyl}-oxime] of erythromycin 0.216 g of sodium hydride as a 50% oil suspension was added portion wise over 5 minutes under argon to a solution of 3 g of the oxime of erythromycin in 80 ml of dry ether in a flask in a bath at 10° C. and then 0.44 ml of 1-chloroethyl ethyl ether were added thereto. The mixture stood at room temperature for 5½ hours and carbon dioxide was bubbled therethrough. The mixture was evaporated to dryness under reduced pressure and the residue was taken up in petroleum ether (b.p.=65°-75° C.). The mixture was stirred for 30 minutes and was vacuum filtered and the product was washed with petroleum ether and dried to obtain 3.54 g of raw product. 3.47 g of the latter were taken up in 17.5 ml of acetone and the suspension was vacuum filtered. The filtrate was stirred with 150 mg of activated carbon for 30 minutes and was then vacuum filtered. The filtrate was treated again with activated carbon and was evaporated to dryness to obtain 3.21 g of product. 2.93 g of the latter and 15 ml of water containing 10% of ethanol was stirred for 30 minutes and was then vacuum filtered. The product was washed with 1.5 ml, 1.0 ml and 1.0 ml of the same solvent and was dried to obtain 2.67 g of 9-[0-{(2-chloroethoxy)-methyl}-oxime] of erythromycin melting at about 129° C. and having a specific rotation of $[\alpha]_D^{20} = -78.5° \pm 3°$ (c=0.5% in chloroform).

Analysis: Calculated: %C, 57.04; %H, 8.74; %N, 3.33; %Cl, 4.21. Found: %C, 56.8; %H, 8.7; %N, 3.2%; %Cl, 4.3.

EXAMPLE 22

9-[0-{(2-dimethylaminoethoxy)-methyl}-oxime] of erythromycin

A mixture of 8.86 g of dimethylamine and 3 g of the product of Example 21 was cooled in an ice bath and after hermetically sealing the flask, it was placed in a bath at 30°-32° C. After complete dissolution, the mixture was held at 30°-32° C. for 74 hours and was then cooled in an ice bath. The flask was opened and the dimethylamine was removed. The residue was dried under reduced pressure to obtain 3.286 g of a white solid and 3.256 g of the latter was taken up in 100 ml of ethyl acetate containing a little ether. The mixture was washed with water six times and with aqueous saturated sodium chloride solution 3 times and the organic phase was dried and evaporated to dryness under reduced pressure to obtain 3.1 g of product. 3 g of the latter and 10 ml of pentane were stirred for 2 hours and the mixture was vacuum filtered. The recovered product was washed and dried to obtain 2.79 g of 9-[0-{(2-dimethylaminoethoxy)-methyl}-oxime] of erythromycin melting at 162° C. and having a specific rotation of $[\alpha]_D^{20} = -78° \pm 2°$ (c=1% in chloroform).

Analysis: Calculated: %C, 59.34; %H, 9.37; %N, 4.94. Found: %C, 59.3; %H, 9.5; %N, 4.6.

EXAMPLE 23

9-[0-{(2-diethylaminoethoxy)-methyl}-oxime] of erythromycin

A mixture of 2.5 g of the product of Example 21 and 10 ml of diethylamine in a hermetically sealed flask was heated at 70° C. for 48 hours and was then allowed to cool to room temperature. The mixture was evaporated to dryness under reduced pressure and the 3.1 g of resin residue was chromatographed over silica gel. Elution was effected with a 6-4-1 toluene-chloroform-triethylamine mixture and the homogenous fractions were evaporated to dryness under reduced pressure and the 1.5 g of white resin were crystallized from 5 ml of isopropyl ether to obtain a first yield of 0.924 g of 9-[0-{(2-diethylaminoethoxy)-methyl}-oxime] of erythromycin in the form of a white powder melting at 135° C. Concentration of the mother liquor yielded an additional 0.22 g of the product melting at 122° C. The product had a specific rotation of $[\alpha]_D^{20} = -74° \pm 1.5°$ (c=1% in chloroform).

Analysis: Calculated: %C, 60.18; %H, 9.53; %N, 4.78. Found: %C, 60.4; %H, 9.6; %N, 4.7.

EXAMPLE 24

9-[0-{(2-aminoethoxy}-methyl)-oxime] of erythromycin

A cooled mixture of 2.5 g of the product of Example 21 and acetone and dry ice was condensed under argon with ammonia until ⅔ of the flask was filled which was then hermetically sealed. The mixture was heated at 50° C. for 20 hours and then cooled in a bath of acetone and dry ice before opening the flask. The ammonia evaporated and the residue was taken up in chloroform. The solution was evaporated to dryness under reduced pressure to obtain 2.3 g of a white resin which was chromatographed over silica gel. Elution with a 9-1 chloroform-trimethylamine mixture was effected and the combined homogenous fractions were evaporated to dryness to obtain 1.3 g of resin. The latter was stirred for 20 minutes with 3 ml of pentane to solidify the product and the mixture was vacuum filtered. The recovered product was rinsed with 0.3 ml of pentane and dried to a constant weight of 0.92 g of 9-[0-{(2-aminoethoxy}-methyl)-oxime] of erythromycin in the form of a white powder melting at 195° C. and having a specific rotation of $[\alpha]_D^{20} = -73° \pm 2°$ (c=1% in chloroform).

Analysis: Calculated: %C, 58.44; %H, 9.19; %N, 5.11. Found: %C, 58.1; %H, 9.3; %N, 4.9.

EXAMPLE 25

9-[0-{(2-methylamino-ethoxy}-methyl)-oxime] of erythromycin

A mixture of 2.5 g of the product of Example 21 and 13.5 g of condensed dimethylamine in a hermetically sealed flask was cooled to −70° C. and the temperature was allowed to rise to room temperature. The mixture was allowed to stand for 41 hours and was then cooled to −70° C. after which the flask was opened. The methylamine evaporated and the product was evaporated to dryness under reduced pressure to obtain 2.7 g of a white resin. The latter was chromatographed over silica gel and was eluted with a 92.5-7.5 chloroform-triethylamine mixture. The combined homogenous fractions were evaporated to dryness under reduced pressure and the 2.2 g of white resin were crystallized from 3 ml of ethanol. The mixture was vacuum filtered and the product was rinsed with 0.3 ml of ethanol and was dried to obtain 1.7 g of 9-[0-{(2-methylamino-ethoxy}-methyl)-oxime] of erythromycin in the form of a white powder melting at 132° C. and having a specific rotation of $[\alpha]_D^{20} = -79° \pm 2°$ (c=1% chloroform).

Analysis: Calculated: %C, 58.9; %H, 9.28; %N, 5.03. Found: %C, 59.1; %H, 9.4; %N, 5.0.

EXAMPLE 26

9-[0-{(2-(morpholin-4-yl)-ethoxy}-methyl)-oxime] of erythromycin 2.5 g of the compound of Example 21 were dissolved with stirring in 10 ml of morphine in a hermetically sealed flask and the solution was stirred at room temperature for 6 days. The mixture was evaporated to dryness to obtain 3 g of white resin which was chromatographed over silica gel. Elution with a 6-4-1 toluene-chloroform-triethylamine mixture yielded homogenous fractions which were evaporated to dryness under reduced pressure to obtain 2.4 g of white resin which was solidified by trituration with 3 ml of a 1-1 pentane-isopropyl ether mixture for 20 minutes. The mixture was vacuum filtered and the product was rinsed with 0.3 ml of the pentane-isopropyl ether mixture and dried to obtain 1.72 g of 9-[0-{(2-(morpholin-4-yl)-ethoxy}-methyl)-oxime] of erythromycin as a white powder melting at 130° C. and having a specific rotation of $[\alpha]_D^{20} = -72° \pm 1.5°$ (c=1% in chloroform).

Analysis: Calculated: %C, 59.24; %H, 9.15; %N, 4.71. Found: %C, 58.9; %H, 9.1; %N, 4.5.

EXAMPLE 27

9-[0-(methylthiomethyl)-oxime] of erythromycin 0.212 g of sodium hydride as a 50% oil suspension was added under argon to a solution of 3 g of the oxime of erythromycin in 80 ml of ether and the mixture was stirred for 15 minutes. A solution of 0.386 g of chloromethyl methyl sulfide in 1 ml of ether was added to the mixture all at once, and after 30 minutes, 8 ml of dimethylformamide were added thereto. After 90 minutes, another 8 ml of dimethylformamide were added to the mixture which stood overnight. Then, 70 mg of sodium hydride and 0.129 g of chloromethyl methyl sulfide were added to the mixture and 90 minutes later, the mixture was saturated with violent bubbling of carbon dioxide therethrough for 90 minutes. 300 ml of aqueous saturated sodium chloride solution were added to the mixture which was vacuum filtered. The product was taken up in chloroform and the solution was washed with aqueous sodium chloride solution, dried and evaporated to dryness to obtain 4.045 g of raw product. The latter was chromatographed over silica gel and was eluted with a 9-1 toluene-triethylamine mixture. The combined homogenous fractions were evaporated to dryness under reduced pressure and the 1.3 g of white resin was crystallized by trituration with 7 ml of petroleum ether (b.p.=65°-75°). The mixture was vacuum filtered and the product was rinsed with 0.7 ml of petroleum ether and dried to obtain 0.93 g of 9-[0-(methylthiomethyl)-oxime] of erythromycin in the form of a white powder melting at 132° C. and having a specific rotation of $[\alpha]_D^{20} = -75.5° \pm 2.5°$ (c=0.45% in chloroform).

Analysis: Calculated: %C, 57.9; %H, 8.97; %N, 3.46; %S, 3.96. Found: %C, 57.6; %H, 8.9; %N, 3.4; %S, 4.0.

EXAMPLE 28

9-[0-(phenylthiomethyl)-oxime] of erythromycin

A solution of 3 g of the oxime of erythromycin, 10 ml of ether and 10 ml of hexamethylphosphotriamide was heated under reduced pressure to evaporate the ether and 0.212 g of sodium hydride as a 50% oil suspension was added portionwise at room temperature under argon to the mixture. The mixture was stirred for 15 minutes and 0.6 ml of chloromethyl phenyl sulfide was added dropwise to the mixture. 70 minutes later, the reaction was stopped by pouring the mixture into 240 ml of aqueous three-fourths saturated sodium chloride solution containing 1 g of sodium bicarbonate. The mixture was stirred for 15 minutes and was then vacuum filtered and the product was rinsed once with water and dissolved in chloroform. The solution was washed with aqueous saturated sodium chloride solution, dried and evaporated to dryness under reduced pressure. The 4.48 g of pale yellow resin were chromatographed over silica gel and was eluted with a 9-1 chloroform-triethylamine mixture. The combined homogenous fractions were evaporated to dryness and the 3.2 g of white resin were crystallized from 10 ml of pentane. The mixture was stirred for 30 minutes at room temperature and was vacuum filtered. The product was rinsed with 0.5 ml of pentane and was dried to obtain 2.39 g of 9-[0-(phenylthiomethyl)-oxime] of erythromycin in the form of a white powder melting at 198° C. and having a specific rotation of $[\alpha]_D^{20} = -2.5° \pm 1°$ (c=0.5% in chloroform).

Analysis: Found: %C, 60.6; %H, 8.6; %N, 3.3; %S 3.7. Calculated: %C, 60.66; %H, 8.56; %N, 3.21; %S, 3.68.

EXAMPLE 29

9-[0-(2,2-dimethoxyethyl)-oxime] of erythromycin

A solution of 3 g of the oxime of erythromycin, 10 ml of ether and 9.6 ml of hexamethylphosphotriamide was heated under reduced pressure to evaporate the ether and the mixture was cooled to room temperature after which 0.212 g of sodium hydride as a 50% oil suspension was added portion-wise thereto. The mixture was stirred for 15 minutes and 0.6 ml of the dimethyl acetal of bromoacetaldehyde was added thereto dropwise. After 2 hours, the reaction was stopped by pouring the mixture into 240 ml of an aqueous three-fourths saturated sodium chloride solution containing 1 g of sodium bicarbonate. The mixture was stirred for 10 minutes and was vacuum filtered and the recovered product was rinsed with an aqueous three-fourths saturated sodium chloride solution and was washed with sufficient chloroform to dissolve the organic component. The filtrate was dried and evaporated to dryness under reduced pressure to obtain 5 g of a white resin which was chromatographed over silica gel. Elution with a 9-1 toluene-triethylamine mixture yielded 3 g of resin which were crystallized from 5 ml of pentane. The mixture was vacuum filtered and the product was rinsed with 0.5 ml of pentane and dried under reduced pressure to obtain 1.912 g of 9-[0-(2,2-dimethoxyethyl)-oxime] of erythromycin melting at first 146° C. and then 186° C. and having a specific rotation of $[\alpha]_D^{20} = -80° \pm 2.5°$ (c=0.6% in chloroform).

Analysis: Calculated: %C, 58.83; %H, 9.15; %N, 3.35. Found: %C, 59.0; %H, 9.3; %N, 3.3.

EXAMPLE 30

9-[0-{(1,3-dioxolan-2-yl)-methyl}-oxime] of erythromycin 0.212 g of sodium hydride as a 50% oil suspension was added portion-wise to a solution of 3 g of the oxime of erythromycin in 60 ml of ether and then 6 ml of dimethylformamide were added thereto. The mixture was stirred for 15 minutes and 0.6 ml of 2-bromomethyl-1,3-dioxolane were added dropwise thereto. After about 3 hours, the ether was evaporated under argon and the mixture was rinsed with one ml of dimethylformamide and was stirred overnight at room temperature. After 19 hours of reaction, 0.106 g of sodium hydride and 0.15 ml of 2-bromomethyl-1,3-dioxolane were added to the mixture and after 5 hours, the reaction was stopped by bubbling carbon dioxide therethrough for one hour. The mixture was poured into 140 ml of an aqueous saturated sodium chloride solution and the mixture was stirred for 10 minutes and was vacuum filtered. The product was solubilized in chloroform and the solution was dried and evaporated to dryness under reduced pressure to obtain 3.7 g of resin. The latter was chromatographed over silica gel and was eluted with a 9-1 toluene-triethylamine mixture. The combined homogenous fractions were evaporated to dryness to obtain 1.55 g of white resin which was solidified by stirring in 5 ml of pentane. The mixture was vacuum filtered and the product was rinsed with 0.5 ml of pentane and dried to obtain 1.227 g of 9-[O-{(1,3-dioxolan-2-yl)-methyl}-oxime] of erythromycin melting first at 140° C. and then at 280° C. and having a specific rotation of $[\alpha]_D^{20} = -67.5° \pm 1.5°$ (c=1% in chloroform).

Analysis: Calculated: %C, 58.91; %H, 8.93; %N, 3.35. Found: %C, 59; %H, 8.9; %N, 3.3.

EXAMPLE 31

9-[0-(2-diethylaminoethyl)-oxime] of erythromycin 1 ml of an aqueous 0.04 M sodium carbonate solution and 2.58 g of 2-chloro-1-diethylaminoethane hydrochloride were added to a solution of 5.62 g of the oxime of erythromycin in 50 ml of tetrahydrofuran and the mixture was refluxed for 16 hours and was filtered. The filtrate was treated with activated carbon and was evaporated to dryness to obtain 6.21 g of raw product. The latter was crystallized from a water-isopropanol mixture to obtain 5.82 g of 9-[0-(2-diethylaminoethyl)-oxime] of erythromycin in the form of colorless crystals melting at ≃220° C. and having a specific rotation of $[\alpha]_D^{20} = -83° \pm 2.5°$ (c=0.7% in ethanol).

Analysis: Calculated: %C, 60.9; %H, 9.6; %N, 4.95. Found: %C, 61.0; %H, 9.8; %N, 4.8.

EXAMPLE 32

9-[0-(2-{pyrrolidin-1-yl}-ethyl)-oxime] of erythromycin 0.720 g of sodium carbonate and 0.76 g of N-(β-chloroethyl)-pyrrolidine were added to a solution of 2.25 g of the oxime of erythromycin in 50 ml of anhydrous acetone and the mixture was refluxed for 6 hours. Then, 40 ml of acetone were added thereto and the mixture was filtered hot. The filtrate was poured into 100 ml of distilled water and the mixture was vacuum filtered. The 2 g of raw product were chromatographed over silica gel and elution with a 9-1 ether-triethylamine mixture yielded 1.72 g of 9-[O-(2{-pyrrolidin-1-yl}-ethyl)oxime] of erythromycin with a specific rotation of $[\alpha]_D^{20} = -83° \pm 2°$ (c=1% in ethanol).

EXAMPLE 33

9-[O-(methoxymethyl)-oxime] of erythromycin 35.3 ml of acetyl chloride were added dropwise at about 20° C. to a stirred mixture of 45 ml of dimethoxymethane and 1.2 ml of anhydrous methanol and the mixture was stirred for 3 days to obtain chloromethyl methyl ether. 2.1 g of sodium bicarbonate and 1.3 g of chloromethyl methyl ether were added to a solution of 3.75 g of the oxime of erythromycin in 75 ml of acetone and the mixture was refluxed for 4 days while adding at 17½ hours and 48 hours 0.45 ml of the said ether. The mixture was poured into 100 ml of water and the mixture was extacted with chloroform. The organic phase was washed with aqueous saturated sodium chloride solution, was dried and evaporated to dryness under reduced pressure. The residue was chromatographed over silica gel and was eluted with a 5-4-1 benzene-chloroform-triethylamine mixture to obtain 2.06 g of 9-[O-(methoxymethyl)-oxime] of erythromycin with a specific rotation of $[\alpha]_D^{20} = -80.5° \pm 2.5°$ (c=0.6% in ethanol).

EXAMPLE 34

9-[O-(2{-piperidin-1-yl}-ethyl)-oxime] of erythromycin 0.72 g of sodium carbonate and 0.830 g of 2-chloroethyl-N-piperidine hydrochloride were added to a solution of 2.25 g of the oxime of erythromycin in 50 ml of anhydrous acetone and the mixture was refluxed for 4 days. 40 ml of acetone were added to the mixture which was then heated to reflux and filtered hot. The filtrate was evaporated to dryness and the residue was chromatographed over silica gel. Elution with a 5-4-1 benzene-chloroform-triethylamine mixture yielded 1.7 g of 9-[O-(2{-piperidin-1-yl}-ethyl)-oxime] of erythromycin with a specific rotation of $[\alpha]_D^{20} = -78° \pm 2.5°$ (c=0.6% in ethanol)

EXAMPLE 35

9-[O-(2-{morpholin-4-yl}-ethyl)oxime] of erythromycin 0.93 g of sodium carbonate and 1.120 g of N-β-chloroethyl-morpholine hydrochloride were added to a solution of 2.25 g of the oxime of erythromycin and 60 ml of acetone and the mixture was refluxed for 6 days. 30 ml of acetone were added to the mixture which was heated to reflux again and was filtered hot. The filtrate was evaporated to dryness under reduced pressure and the residue was taken up in cold acetone. The mixture was filtered and the filtrate was concentrated to a small volume. Ether was added thereto and the mixture was vacuum filtered. The product was dried to obtain 1.45 g of 9-[O-(2-{morpholin-4-yl}-ethyl)-oxime] of erythromycin with a specific rotation of $[\alpha]_D^{20} = -73.5° \pm 3°$ (c=0.5% in ethanol).

Analysis: $C_{43}H_{79}N_3O_{14}$; molecular weight=862.112; Calculated: %C, 59.9; %H, 9.2; %N, 4.87. Found: %C, 59.9; %H, 9.3; %N, 4.7.

EXAMPLE 36

9-[O-(2-dimethylamino-1-methyl-ethyl)-oxime] of erythromycin 6.4 g of sodium carbonate and 6.35 g of 2-chloro-1-dimethylamino-propane were added to a solution of 20 g of the oxime of erythromycin in 300 ml of acetone and the mixture was refluxed for 3 days. 100 ml of acetone were added to the mixture which was filtered. The filtrate was treated with activated carbon and 500 ml of water were added thereto. The mixture was filtered to obtain 19.8 g of 9-[O-(2-dimethylamino-1-methyl-ethyl)-oxime] of erythromycin with a specific rotation of $[\alpha]_D^{20} = -96°$ (c=0.75% in ethanol).

Analysis: $C_{42}H_{79}N_3O_{13}$; molecular weight=834.10; Calculated: %C, 60.48; %H, 9.54; %N, 5.03. Found: %C, 60.3; %H, 9.6; %N, 5.0.

EXAMPLE 37

9-[O-(3-dimethylamino-propyl)-oxime] of erythromycin 1.2 g of sodium carbonate and 1.22 g of 3-chloro-1-dimethylamino-propane hydrochloride were added to a solution of 3.75 g of the oxime of erythromycin in 40 ml of anhydrous acetone and the mixture was refluxed for 7 days. 50 ml of acetone were added to the mixture which was heated again to reflux and filtered hot. The filtrate was concentrated to a volume of 5 ml and 100 ml of petroleum ether (b.p.=60°–80° C.) were added. The mixture was vacuum filtered and the product was dissolved in about 60 ml of acetone. The soluton was treated with activated carbon at 40° C. and was filtered. The filtrate was concentrated to a small volume and little by little petroleum ether (b.p.=60°–80° C.) was added thereto. The mixture was cooled to room temperature and was vacuum filtered to obtain 1.30 g of 9-[O-(3-dimethylamino-propyl)oxime] of erythromycin with a specific rotation of $[\alpha]_D^{20} = -70° \pm 2°$ (c=1% in chloroform).

Analysis: $C_{42}H_{79}N_3O_{13}$; molecular weight=834.109; Calculated: %C, 60.5; %H, 9.5; %N, 5.0. Found: %C, 60.6; %H, 9.7; %N, 4.9.

EXAMPLE 38

9-[O-(2-bromoethyl)-oxime] of erythromycin 0.75 g of sodium hydride was added to a mixture of 5.62 g of the oxime of erythromycin and 100 ml of ether and after the evolution of gas ceased, 15 ml of 1,2-dibromoethane were added thereto. The mixture was refluxed for 16 hours and was then cooled to 20° C. and 0.75 g of sodium hydride were added. The mixture was refluxed for another 6 hours and after cooling the mixture to about 0° C., 100 ml of methylene chloride were added thereto. 3 ml of acetic acid were added dropwise with stirring to the mixture and after the temperature returned to room temperature, the mixture was poured into 50 ml of water containing 4 ml of 28% ammonium hydroxide. The aqueous phase was extracted with methylene chloride and the combined organic phases were washed with water, dried and evaporated to dryness. The residue was chromatographed over silica gel and was eluted with a 25-0.5 methylene chloride-triethylamine mixture to obtain 4.78 g of 9-[O-(2-bromoethyl)-oxime] of erythromycin with a specific rotation of $[\alpha]_D^{20} = -87° \pm 2.5°$ (c=0.5% in ethanol).

Analysis: $C_{39}H_{71}BrN_2O_{13}$; molecular weight=855.9; Calculated: %C, 54.7; %H, 8.3; %N, 3.27; %Br, 9.3. Found: %C, 54.6; %H, 8.3; %N, 3.2; %Br, 9.2.

EXAMPLE 39

9-[O-(2-isopropylamino)-oxime] of erythromycin

A mixture of 2.58 g of 9-[O-(2-bromoethyl)-oxime] of erythromycin and 12 ml of isopropylamine was stirred under an inert atmosphere at room temperature for 15 hours and the mixture was then poured into 600 ml of water. The mixture was filtered and the recovered product was washed with water and dried to obtain 2.29 g of raw product. The latter was chromatographed over silica gel and was eluted with a 25-0.5 methylene chloride-triethylamine mixture to obtain 1.60 g of 9-[O-(2-isopropylamino)-oxime] of erythromycin with a specific rotation of $[\alpha]_D^{20} = -78.5°$ (c=0.5% in ethanol).

Analysis: $C_{42}H_{79}N_3O_{13}$; molecular weight=834; Calculated: %C, 60.5; %H, 9.55; %N, 5.04. Found: %C, 60.6; %H, 9.5; %N, 4.9.

EXAMPLE 40

9-[O-{(isobutoxy)-methyl}-oxime] of erythromycin 2.52 g of sodium bicarbonate and 0.76 g of chloromethyl isobutyl ether were added to a solution of 4.49 g of the oxime of erythromycin in 40 ml of acetone and the mixture was refluxed for 41 hours while adding at 18 hours and 26 hours 0.4 ml of chloromethyl isobutyl ether. The mixture was filtered and the filtrate was evaporated to dryness. The residue was taken up in 20 ml of aqueous saturated sodium bicarbonate solution and the mixture was vacuum filtered. The product was chromatographed over silica gel and eluted with a 15-1 benzene-triethylamine mixture to obtain 3.07 g of 9-[O-{(isobutoxy)-methyl}-oxime] of erythromycin with a specific rotation of $[\alpha]_D^{20} = -79.5° \pm 3°$ (c=0.5% in ethanol).

Analysis: $C_{42}H_{78}N_2O_{14}$; molecular weight=835; Calculated: %C, 60.4; %H, 9.4; %N, 3.35. Found: %C, 60.7; %H, 9.7; %N, 3.5.

EXAMPLE 41

9-[O-(2-disopropylamino-ethyl)-oxime] of erythromycin 5.04 g of sodium bicarbonate and 1.25 g of 2-chloro-1-diisopropylamino-ethane hydrochloride were added to a solution of 5.62 g of the oxime of erythromycin in 50 ml of tetrahydrofuran and the mixture was refluxed for 4 days while adding at the 64th hour 0.82 g of 2-chloro-1-diisopropylamino-ethane hydrochloride. The mixture was filtered and the filtrate was evaporated to dryness. The residue was chromatographed over silica gel and was eluted with a 25-0.5 methylene chloride-triethylamine mixture to obtain 4.37 g of 9-[O-(2-diisopropylamino-ethyl)-oxime] of erythromycin with a specific rotation of $[\alpha]_D^{20} = -73° \pm 3°$ (c=0.5% in ethanol).

Analysis: $C_{45}H_{85}N_3O_{13}$; molecular weight=876; Calculated: %C, 61.7; %H, 9.8; %N, 4.8. Found: %C, 61.7; %H, 9.9; %N, 4.7.

EXAMPLE 42

9-[O-(2-{diethoxy}-ethyl)-oxime] of erythromycin 0.4 g of sodium hydride as a 50% oil suspension was added to a solution of 5.62 g of the oxime of erythromycin, 18 ml of hexamethylphosphotriamide and 5 ml of ether and after stirring the mixture for 15 minutes, 1.55 ml of the diethylacetal of bromoacetaldehyde were added dropwise to the mixture. The mixture was stirred for 3½ hours at 20° C. and was then poured into 500 ml of an aqueous sodium chloride solution containing 2 g of sodium bicarbonate. The mixture was extracted with ether and the ether phase was washed with aqueous sodium chloride, dried and evaporated to dryness under reduced pressure. The 6.35 g of residue were chromatographed over silica gel and was eluted with a 9-1 benzene-triethylamine mixture and then with a 7-2-1 benzene-chloroform-triethylamine mixture to obtain 1.7 g of 9-[O-(2-{diethoxy}-ethyl)oxime] of erythromycin with a specific rotation of $[\alpha]_D^{20} = -75.5° \pm 2.5°$ (c=0.65% in ethanol).

Analysis: $C_{43}H_{80}N_2O_{15}$; molecular weight=865.120; Calculated: %C, 59.70; %H, 9.32; %N, 3.23. Found: %C, 60.1; %H, 9.4; %N, 3.3.

EXAMPLE 43

9-[O-(2-{4-methyl-piperazino-1-yl}-ethyl)-oxime] of erythromycin

A solution of 2.31 g of the product of Example 38 in 10 ml of N-methyl-piperazine was stirred at 20° C. for 20 hours and was then poured into 50 ml of water containing 0.5 g of potassium carbonate. The mixture was filtered and the recovered product was washed with water and dried to obtain 1.99 g of product which was dissolved in methylene chloride. The solution was washed with aqueous sodium carbonate solution, dried and evaporated to dryness. The residue was taken up in isopropyl ether and the solution was filtered. The filtrate was evaporated and the residue was washed with pentane to obtain 0.94 g of 9-[O-(2-{-4-methyl-piperazine-1-yl}ethyl)-oxime] of erythromycin with a specific rotation of $[\alpha]_D^{20} = -81° \pm 2°$ (c=1% in ethanol).

Analysis: $C_{44}H_{82}N_4O_{13}$; molecular weight=875.2; Calculated: %C, 60.4; %H, 9.45; %N, 6.40. Found: %C, 60.5; %H, 9.4; %N, 6.2.

EXAMPLE 44

9-[O-(2-ethylamino-ethyl)-oxime] of erythromycin 2.31 g of the product of Example 38 were placed in a 50 ml flask and were cooled with an acetone-dry ice mixture while monoethylamine was added to fill the flask to ⅔ of its capacity after which the flask was hermetically sealed. The mixture was stirred at room temperature for 20 hours and was then cooled and the flask opened. The ethylamine was evaporated and the residue was taken up in water. The solution was filtered and the recovered product was washed with water and dried to obtain 2.3 g of raw product. The latter was chromatographed over silica gel and was eluted with a 25-0.5 methylene chloride-triethylamine mixture to obtain 1.76 g of 9-[O-(2-ethylamino-ethyl)-oxime] of erythromycin with a specific rotation of $[\alpha]_D^{20} = -82° \pm 2°$ (c=1% in ethanol).

Analysis: $C_{41}H_{77}N_3O_{13}$; molecular weight=820; Calculated: %C, 60.05; %H, 9.47; %N, 5.12. Found: %C, 60.5; %H, 9.5; %N, 4.7.

EXAMPLE 45

9-[O-(2-aminoethyl)-oxime] of erythromycin 20 ml of ammonia were added to 4.5 g of the product of Example 38 in a 50 ml flask cooled with an acetone-dry ice mixture and the flask was hermetically sealed. The mixture was stirred at 20° C. for 68 hours and was then cooled and the flask was opened. The ammonia was evaporated and the residue was taken up in methylene chloride. The solution was washed with water, dried and evaporated to dryness to obtain 3.97 g of residue. The latter was chromatographed over silica gel and was eluted with a 19-1 methylene chloride-triethylamine mixture. The product was taken up in methylene chloride and the solution was washed with aqueous sodium carbonate solution, dried and evaporated to dryness. The residue was chromatographed again over silica gel and was eluted with a 15-1 chloroform-triethylamine mixture to obtain 1.67 g of 9-[O-(2-aminoethyl)-oxime] of erythromycin with a specific rotation of $[\alpha]_D^{20} = -76° \pm 2°$ (c=0.8% in ethanol).

Analysis: $C_{39}H_{73}N_3O_{13}$; molecular weight=792; Calculated: %C, 59.1; %H, 9.3; %N, 5.3. Found: %C, 59.4; %H, 9.4; %N, 5.2.

EXAMPLE 46

9-[O-(2-diethylamino-isopropyl)-oxime] of erythromycin 0.64 g of sodium carbonate and then 0.8 g of 1-diethylamino-2-chloro-propane hydrochloride were added to a solution of 2 g of the oxime of erythromycin and 30 ml of acetone and the mixture was refluxed for 23 hours. The mixture was filtered and water was added to the filtrate. The mixture was vacuum filtered and the product was washed with a water-acetone mixture and was dried to obtain 1.9 g of 9-[O-(2-diethylamino-isopropyl)-oxime] of erythromycin with a specific rotation of $[\alpha]_D^{20} = -84° \pm 2.5°$ (c=0.75% in ethanol).

Analysis: $C_{44}H_{83}N_3O_{13}$; molecular weight=862.164; Calculated: %C, 61.3; %H, 9.7; %N, 4.87. Found: %C, 61.4; %H, 9.7; %N, 4.8.

EXAMPLE 47

9-[0-(oxiramylmethyl)-oxime] of erythromycin 354 mg of sodium hydride as a 50% oil suspension were slowly added to a solution of 5 g of the oxime of erythromycin in 23 ml of dimethylformamide and after stirring the mixture for 15 minutes, a solution of 1 g of epibromohydrin in 1 ml of dimethylformamide was added dropwise thereto. The mixture was neutralized by bubbling carbon dioxide therethrough and was then poured into 250 ml of an aqueous saturated sodium chloride solution. The mixture was stirred for 10 minutes and was vacuum filtered and the product was rinsed with water and dissolved in chloroform. The organic phase was dried, treated with activated carbon and evaporated to dryness. The residue was crystallized from pentane and the 4.1 g of raw product was chromatographed over silica gel. Elution with a 9-1 chloroform-triethylamine mixture yielded after crystallization from pentane 0.87 g of 9-[0-(oxiramylmethyl)-oxime] of erythromycin melting at 154° C. and having a specific rotation of $[\alpha]_D^{20} = -79° \pm 2.5°$ (c=0.5% in chloroform).

Analysis: $C_{40}H_{72}N_2O_{14}$; molecular weight=805; Calculated: %C, 59.68; %H, 9.01; %N, 3.48. Found: %C, 59.6; %H, 9.1; %N, 3.5.

EXAMPLE 48

9-[0-(3-dimethylamino-2-hydroxy-propyl)-oxime] of erythromycin 2.5 g of the product of Example 47 were placed in a hermetically sealed flask cooled in an ice bath and 2.8 g of dimethylamine were rapidly thereto and the flask was sealed. The mixture was stirred at 20° C. for 250 minutes and was then cooled and the flask was opened. The dimethylamine was evaporated and the residue was chromatographed over silica gel. Elution with a 9-1 chloroform-triethylamine mixture yielded after crystallization from pentane and drying 1.21 g of 9-[0-(3-dimethylamino-2-hydroxy-propyl)-oxime] of erythromycin melting at 144° C. and having a specific rotation of $[\alpha]_D^{20} = -84.5° \pm 2.5°$ (c=0.6% in chloroform).

Analysis: $C_{42}H_{79}N_3O_{14}$; molecular weight=850.10; Calculated: %C, 59.34; %H, 9.37; %N, 4.94. Found: %C, 59.1; %H, 9.4; %N, 4.8.

EXAMPLE 49

9-[0-(2-diethylamino-ethyl)-oxime] of erythromycin 4.5 g of a different isomer of the oxime of erythromycin than than of Example 31 were dissolved in 45 ml of tetrahydrofuran and 2.6 g of sodium carbonate and then 2.1 g of diethylaminoethyl chloride hydrochloride were added thereto. The mixture was refluxed for 5 ½ hours and was filtered. The filtrate was evaporated to dryness and the residue was chromatographed over silica gel. Elution with a 5-4-1 benzene-chloroform-triethylamine mixture and then with a 15-1 methylene chloride-triethylamine mixture yielded 0.5 g of 9-[0-(2-diethylamino-ethyl)-oxime] of erythromycin with a specific rotation of $[\alpha]_D^{20} = -52° \pm 2.5°$ (c=0.5% in ethanol) which was the other isomer of the product of Example 31.

Analysis: $C_{43}H_{81}N_3O_{13}$: Calculated: %C, 60.89; %H, 9.62; %N, 4.95. Found: %C, 61.2; %H, 9.7; %N, 4.9.

EXAMPLE 50

Tablets were prepared containing 0.5 g of the product of Example 31 or 0.2 g of the product of Example 1 and sufficient excipient of starch, talc and magnesium stearate for a final weight of 1 g.

PHARMACOLOGICAL STUDY

A. In Vitro Activity

The method was a serial dilution of liquid medium test wherein a series of tubes were prepared containing the same amount of sterile nutritive medium and increasing amounts of the test product was distributed in each tube. The tubes were then seeded with a bacterial strain and incubated for 24 hours in an oven at 37° C. The degree of inhibition was determined by transillumination to determine the minimum inhibiting concentration (MIC) express in µg/ml and the results are reported in the following Tables.

| STRAIN | PRODUCT OF EXAMPLE MIC in µg/ml | | | | | |
|---|---|---|---|---|---|---|
| | Ex 1 et 6 | Ex 2 | Ex 3 | Ex 4 | Ex 5 | Ex 7 |
| Staphylococcus aureus ATCC 6538 Pen-Sensibles | 0,5 | 0,1 | 0,5 | 2 | 1 | 0,2 |
| Staphylococcus aureus UC 1 128 Pen-Resistant | 2 | 1 | 1 | 3 | 1 | 1 |
| Staphylococcus aureus exp. n° 54 146 | 1 | 0,5 | 0,5 | 2 | 1 | 0,5 |
| Streptococcus pyogenes A 561 | 0,05 | ≦0,02 | 0,1 | 0,05 | ≦0,02 | 0,05 |
| Streptococcus faecalis 5 432 | 0,2 | 0,1 | 0,2 | 0,5 | 0,05 | 0,1 |
| Streptococcus faecalis 99 F 74 | 0,2 | 0,1 | 0,2 | 0,2 | 0,05 | 0,1 |
| Bacillus subtilis ATCC 6 633 | 0,2 | 0,2 | 0,2 | 0,5 | 0,5 | 0,1 |

| STRAIN | PRODUCTS OF EXAMPLES MIC in µg/ml | | | | | | | | | |
|---|---|---|---|---|---|---|---|---|---|---|
| | 13 | 14 | 15 | 16 | 17 | 20 | 21 | 22 | 23 | 24 | 25 |
| Staphylococcus aureus 1061 pen-sensibles | 0,4 | 0,2 | 0,6 | 0,4 | 0,4 | 0,4 | 0,2 | 0,4 | 0,4 | 0,1 | 0,5 |
| Staphylococcus aureus UC 1128 pen-resistant | 0,6 | 0,4 | 1 | 0,6 | 0,6 | 0,6 | 0,2 | 0,6 | 1 | 0,4 | 0,5 |
| Staphylococcus aureus exp. 54 146 | 0,4 | 0,4 | 0,6 | 0,4 | 0,4 | 0,4 | 0,2 | 0,4 | 0,6 | 0,4 | 0,5 |
| Streptococcus pyogenes A 561 | 0,02 | 0,02 | 0,1 | 0,05 | 0,05 | 0,1 | 0,02 | ≦0,01 | 0,02 | ≦0,01 | ≦0,01 |
| Streptococcus faecalis 5432 | 0,01 | 0,1 | 0,1 | 0,2 | 0,1 | 0,1 | 0,1 | 0,05 | 0,1 | 0,05 | 0,05 |
| Streptococcus faecalis 99 F 74 | 0,1 | 0,05 | 0,2 | 0,1 | 0,1 | 0,1 | 0,1 | 0,05 | 0,1 | 0,1 | 0,05 |
| Streptococcus faecalis 5435 | 0,4 | 0,4 | 0,6 | 1 | 0,6 | 0,2 | — | 0,2 | 0,2 | 0,2 | 0,2 |

| STRAIN | PRODUCTS OF EXAMPLES MIC in µg/ml | | | | | | | | | |
|---|---|---|---|---|---|---|---|---|---|
| | 26 | 28 | 29 | 30 | 31 | 32 | 33 | 34 | 35 | 36 |
| Staphylococcus aureus 1061 pen-sensibles | 0,6 | 0,4 | 0,4 | 0,4 | 0,5 | 0,4 | 0,1 | 0,4 | 0,4 | 0,2 |
| Staphylococcus aureus UC 1128 pen-resistant | 0,1 | 0,6 | 1 | 0,6 | 1 | 1 | 0,4 | 0,6 | 1 | 0,5 |
| Staphylococcus aureus exp. 54 146 | 0,6 | 0,6 | 0,4 | 0,4 | 1 | 0,6 | 0,2 | 0,6 | 0,6 | 0,5 |
| Streptococcus pyogenes A 561 | 0,1 | 0,05 | 0,1 | 0,05 | 0,02 | ≦0,01 | 0,02 | ≦0,01 | 0,05 | ≦0,01 |
| Streptococcus faecalis 5432 | 0,2 | 0,2 | 0,4 | 0,4 | 0,1 | 0,05 | 0,1 | 0,1 | 0,2 | 0,1 |
| Streptococcus faecalis 99 F 74 | 0,2 | 0,2 | 0,2 | 0,2 | 0,1 | 0,1 | 0,1 | 0,05 | 0,4 | 0,1 |
| Streptococcus faecalis 5435 | 1 | 0,4 | 1 | 2 | — | 0,2 | 0,2 | 0,2 | 1 | 0,5 |

| STRAIN | PRODUCTS OF EXAMPLES MIC in µg/ml | | | | | | |
|---|---|---|---|---|---|---|---|
| | 39 | 41 | 43 | 45 | 46 | 47 | 48 |
| Staphylococcus aureus 1061 pen-sensibles | 0,3 | 0,5 | 1 | 0,6 | 0,2 | 0,2 | 0,4 |
| Staphylococcus aureus UC 1128 pen-resistant | 0,6 | 1 | 2 | 1 | 0,6 | 0,4 | 0,6 |
| Staphylococcus aureus exp. 54 146 | 0,4 | 1 | 1 | 1 | 0,4 | 0,4 | 0,6 |
| Streptococcus pyogenes A 561 | 0,01 | 0,05 | ≦0,01 | ≦0,01 | ≦0,01 | 0,05 | 0,05 |
| Streptococcus faecalis 5432 | 0,05 | 0,2 | 0,2 | 0,4 | 0,05 | 0,2 | 0,4 |
| Streptococcus faecalis 99 F 74 | ≦0,02 | 0,2 | 0,05 | 0,1 | 0,05 | 0,2 | 0,1 |
| Streptococcus faecalis 5435 | 0,1 | — | 0,4 | 0,2 | 0,1 | 0,2 | 1 |

B. In Vivo Activity

The test was effected with the compounds of the invention and erythromycin as a reference on groups of 10 mice weighing about 21 g experimentally infected with Staphylococcus aureus No. 54,146 by intraperitoneal administration of 0.5 ml of a 22 hour culture of the said organism in bouillon with a pH of 7 diluted to 1/6 with physiological water. The test compounds were orally administrated to the mice 1,5 and 24 hours after the infection and the mortality on the 8th day was determined. The results are reported in the following Table.

| PRODUCT of EXAMPLE | No. of mice living on the 8th day DOSES in mg | | | | | |
|---|---|---|---|---|---|---|
| | 0,25mg | 0,5mg | 0,75mg | 1mg | 1,5mg | 2mg |
| 1 | 7 | 10 | | | | |
| 3 | | 7 | 9 | 9 | | |
| 4 | 0 | 4 | 9 | 10 | | |
| 5 | 2 | 8 | 10 | | | |
| 15 | 1 | 9 | 10 | | | |
| 20 | 2 | 4 | 10 | | | |
| 21 | 0 | 6 | 10 | | | |
| 29 | 2 | 8 | 9 | 10 | | |
| 30 | 2 | 7 | 10 | | | |
| 31 | 4 | 10 | | | | |
| 33 | 7 | 10 | | | | |
| 35 | 2 | 8 | 9 | 10 | | |
| 36 | 3 | 9 | 10 | | | |
| 41 | 9 | 10 | | | | |
| Erythromycin | | | 5 | 9 | 9 | 10 |

In a second test, groups of 10 male mice weighing about 21 g were experimentally infected by an intraperitoneal injection of 0.5 ml of a 22 hour culture of Streptococcus pyrogenes A561 in Todd Hewitt bouillon with a pH of 7 diluted to 1/1000 with physiological water. The compounds of Examples 1 or 5 were administered orally 1,5 and 24 hours after the infection and the number of mice living on the fifth day was determined. The results are reported in the following Table.

TABLE

| Product of Example | Dose in mg | No. of mice alive on 5th day |
|---|---|---|
| 1 | 0.1 | — |
| | 0.5 | 2 |
| | 1 | 10 |
| 5 | 0.1 | 10 |
| | 0.5 | — |
| | 1.0 | — |

Various modifications of the products and processes of the invention may be made without departing from the spirit or scope thereof and it should be understood that the invention is intended to be limited only as defined in the appended claims.

What we claim is:

1. An erythromycin compound selected from the group consisting of a compound in the syn form or antiform or mixtures of the syn and anti forms of the formula

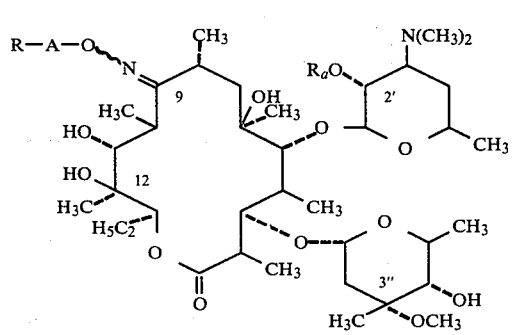

wherein A is a linear or branched alkylene of 1 to 6 carbon atoms, R is selected from the group consisting of optionally substituted alkoxy of 1 to 6 carbon atoms, optionally substituted alkenyloxy and alkynyloxy of 2 to 6 carbon atoms, optionally substituted alkylthio of 1 to 6 carbon atoms, optionally substituted alkenylthio and alkynyllthio of 2 to 6 carbon atoms with the thio groups optionally oxidized to the sulfoxide or sulfone form, optionally substituted aryloxy and arylthio, optionally substituted aralkyloxy and arylalkylthio of 1 to 6 alkyl carbon atoms the thio derivatives optionally oxidized to sulfoxide or sulfone

optionally substituted quaternary ammonium group, halogen, optionally substituted 1,2-epoxyethyl and the group resulting from opening of the epoxy with a nucleophilic reactant,

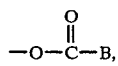

a free or protected formyl, —COOR', thiocyanate, —CN, acyl and carbamoy, the said optional substitutents on the R groups being at least one member of the group consisting of halogen and alkoxy and alkylthio of 1 to 6 carbon atoms $R_1$ and $R_2$ are individually selected from the group consisting of hydrogen and optionally substituted alkyl of 1 to 6 carbon atoms or taken together with the nitrogen atom to which they are attached form an optionally substituted, optionally unsaturated heterocycle which can contain another heteroatom, B is selected from the group consisting of optionally substituted alkyl and alkoxy of 1 to 6 carbon atoms, optionally substituted aryl and aryloxy and optionally substituted aralkyl and aralkoxy of 1 to 6 alkyl carbon atoms, R' is selected from the group consisting of hydrogen, a cation and an ester group, $R_a$ is selected from the group consisting of hydrogen and acyl of an organic carboxylic acid of 1 to 18 carbon atoms and their nontoxic, pharmaceutically acceptable acid addition salts.

2. A compound of claim 1 wherein R is selected from the group consisting of halogen, dialkylamino, alkoxy optionally substituted with alkoxy or dialkylamino, aryloxy or aralkoxy optionally substituted with a halogen and alkylthio or aryl alkylthio optionally substituted with a halogen.

3. A compound of claim 1 having the formula wherein n is an integer from 1 to 6, R' is selected from the group consisting of alkoxy and alkoxyalkoxy of 1 to 6 carbon atoms, phenoxy or benzyloxy optionally substituted with a chlorine and dialkylamino of 1 to 7 alkyl carbon atoms and $R_a'$ is selected from the group consisting of hydrogen and acyl of an alkanoic acid of 2 to 6 carbon atoms and their non-toxic, pharmaceutically acceptable acid addition salts.

4. A compound of claim 3 wherein R' is selected from the group consisting of $CH_3—(CH_2)_{n1}—O—$ and $CH_3—(CH_2)_{n1}—O—(CH_2)_{n2}—O—$ and $n_1$ is an integer from 0 to 3 and $n_2$ is an integer from 1 to 3.

5. A compound of claim 3 wherein R' is

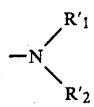

and $R_1'$ and $R_2'$ are individually alkyl of 1 to 3 carbon atoms.

6. A compound of claim 1 selected from the group consisting of 9-[O-({2-methoxy-ethoxy}-methyl)-oxime] of erythromycin, 9-[O-(2-dimethylamino-ethyl)-oxime] of erythromycin, 9-[O-(2-diethylamino-ethyl)-oxime] of erythromycin and their non-toxic, pharmaceutically acceptable acid addition salts.

7. An antibiotic composition comprising an antibiotically effective amount of at least one compound of claim 1 and an inert pharmaceutical carrier.

8. A composition of claim 7 wherein R is selected from the group consisting of halogen, dialkylamino, alkoxy optionally substituted with alkoxy or dialkylamino, aryloxy or aralkoxy optionally substituted with a halogen and alkylthio or aryl alkylthio optionally substituted with a halogen.

9. A composition of claim 7 wherein the compound has the formula

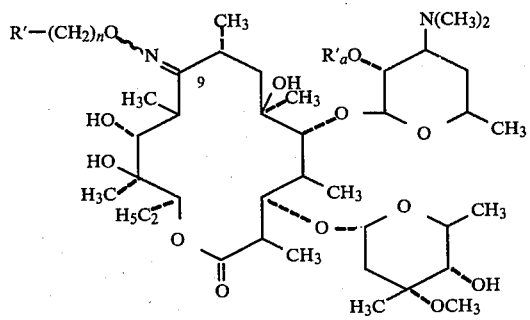

wherein n is an integer from 1 to 6, R' is selected from the group consisting of alkoxy and alkoxyalkoxy of 1 to 6 carbon atoms, phenoxy or benzyloxy optionally substituted with a chlorine and dialkylamino of 1 to 7 alkyl carbon atoms and $R_a'$ is selected from the group consisting of hydrogen and acyl of an alkanoic acid of 2 to 6 carbon atoms and their non-toxic, pharmaceutically acceptable acid addition salts.

10. A composition of claim 9 wherein R' is selected from the group consisting of $CH_3—(CH_2)_{n1}—O—$ and $CH_3—(CH_2)_{n1}—O—(CH_2)_{n2}—O—$ and $n_1$ is an integer from 0 to 3 and $n_2$ is an integer from 1 to 3.

11. A composition of claim 9 wherein R' is

and $R_1'$ and $R_2'$ are individually alkyl of 1 to 3 carbon atoms.

12. A composition of claim 7 selected from the group consisting of 9-[O-({2-methoxy-ethoxy}-methyl)-oxime] of erythromycin, 9-[O-(2-dimethylamino-ethyl)-oxime] of erythromycin, 9-[O-(2-diethylamino-ethyl)-oxime] of erythromycin and their non-toxic, pharmaceutically acceptable acid addition salts.

13. A method of combatting bacterial infections in warm-blooded animals comprising administering to warm-blooded animals an antibacterically effective amount of at least one compound of claim 1.

14. A method of claim 13 wherein R is selected from group consisting of halogen, dialkylamino, alkoxy optionally substituted with alkoxy or dialkylamino, aryloxy or aralkoxy optionally substituted with a halogen and alkylthio or aryl alkylthio optionally substituted with a halogen.

15. A method of claim 13 wherein the compound has the formula

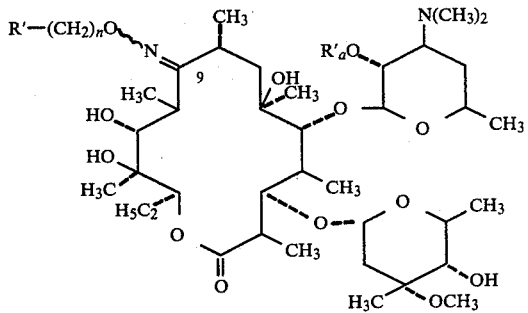

wherein n is an integer from 1 to 6, R' is selected from the group consisting of alkoxy and alkoxyalkoxy of 1 to 6 carbon atoms, phenoxy or benzyloxy optionally substituted with a chlorine and dialkylamino of 1 to 7 alkyl carbon atoms and $R_a'$ is selected from the group consisting of hydrogen and acyl of an alkanoic acid of 2 to 6 carbon atoms and their non-toxic, pharmaceutically acceptable acid addition salts.

16. A method of claim 15 wherein R' is selected from the group consisting of $CH_3—(CH_2)_{n1}—O—$ and $CH_3(CH_2)_{n1}—O—(CH_2)_{n2}—O—$ and $n_1$ is an integer from 0 to 3 and $n_2$ is an integer from 1 to 3.

17. A method of claim 15 wherein R' is

and $R_1'$ and $R_2'$ are individually alkyl of 1 to 3 carbon atoms.

18. A method of claim 13 wherein the compounds are selected from the group consisting of 9-[O-({2-methoxy-ethoxy}-methyl)-oxime] of erythromycin, 9-[O-(2-dimethylamino-ethyl)-oxime] of erythromycin, 9-[O-(2-diethylamino-ethyl)-oxime] of erythromycin and their non-toxic, pharmaceutically acceptable acid addition salts.

* * * * *